United States Patent [19]

Morisawa et al.

[11] Patent Number: 5,346,918
[45] Date of Patent: Sep. 13, 1994

[54] MILBEMYCIN ETHER DERIVATIVES, THEIR PREPARATION AND THEIR THERAPEUTIC AND AGROCHEMICAL USES

[75] Inventors: Yasuhiro Morisawa; Akio Saito; Toshimitsu Toyama; Susumu Kaneko, all of Tokyo, Japan

[73] Assignee: Sankyo Company Limited, Tokyo, Japan

[21] Appl. No.: 661,833

[22] Filed: Feb. 27, 1991

[30] Foreign Application Priority Data

Mar. 1, 1990 [JP] Japan .................. 2-50760

[51] Int. Cl.$^5$ .................. A61K 31/365; C07D 325/00
[52] U.S. Cl. .................. 514/450; 549/264
[58] Field of Search .................. 549/264; 514/450

[56] References Cited

U.S. PATENT DOCUMENTS

| | | | |
|---|---|---|---|
| 3,950,360 | 4/1976 | Aoki et al. | 549/264 |
| 4,171,314 | 10/1979 | Chabala et al. | 536/7.1 |
| 4,173,571 | 11/1979 | Chabala et al. | 536/7.1 |
| 4,199,569 | 4/1980 | Chabala et al. | 536/7.1 |
| 4,200,581 | 4/1980 | Fisher et al. | 536/7.1 |
| 4,201,861 | 5/1980 | Mrozik et al. | 536/7.1 |
| 4,203,976 | 5/1980 | Fisher et al. | 536/7.1 |
| 4,206,205 | 6/1980 | Mrozik et al. | 536/7.1 |
| 4,289,760 | 9/1981 | Mrozik et al. | 536/7.1 |
| 4,346,171 | 8/1982 | Takiguchi et al. | 549/264 |
| 4,423,209 | 12/1983 | Mrozik | 549/264 |
| 4,457,920 | 7/1984 | Mrozik | 536/7.1 |
| 4,547,491 | 10/1985 | Mrozik et al. | 549/264 |
| 4,547,520 | 10/1985 | Ide et al. | 549/264 |
| 4,579,864 | 4/1986 | Linn et al. | 549/264 |
| 4,696,945 | 9/1987 | Frei et al. | 549/264 |
| 4,959,386 | 9/1990 | Frei et al. | 549/214 |

FOREIGN PATENT DOCUMENTS

| | | |
|---|---|---|
| 0008184 | 7/1979 | European Pat. Off. . |
| 0102721 | 7/1983 | European Pat. Off. . |
| 0115930 | 1/1984 | European Pat. Off. . |
| 0170006 | 6/1985 | European Pat. Off. . |
| 0180539 | 9/1985 | European Pat. Off. . |
| 0184989 | 11/1985 | European Pat. Off. . |
| 0184173 | 6/1986 | European Pat. Off. . |
| 0203832 | 6/1986 | European Pat. Off. . |
| 0186043 | 7/1986 | European Pat. Off. . |
| 0357460 | 3/1990 | European Pat. Off. . |
| 57-120587 | 7/1982 | Japan . |
| 57-120589 | 7/1982 | Japan . |
| 59-16894 | 1/1984 | Japan . |
| 2176182 | 4/1986 | United Kingdom . |

OTHER PUBLICATIONS

J. Antimicrob, Agents & Chemother. 15(3) 361–367 (1979).

*Primary Examiner*—C. Warren Ivy
*Assistant Examiner*—A. A. Owens
*Attorney, Agent, or Firm*—Frishauf, Holtz, Goodman & Woodward

[57] ABSTRACT

Compounds of formula (I):

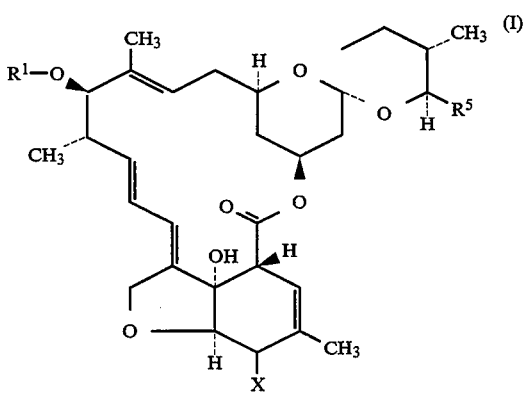

in which: $R^1$ is a variety of organic groups; $R^5$ is methyl, ethyl, isopropyl or sec-butyl; and X is hydroxy, alkanoyloxy or hydroxyimino and salts and esters thereof have valuable anthelmintic, acaricidal and insecticidal activities. Methods of preparing the compounds are also provided.

17 Claims, No Drawings

MILBEMYCIN ETHER DERIVATIVES, THEIR PREPARATION AND THEIR THERAPEUTIC AND AGROCHEMICAL USES

BACKGROUND TO THE INVENTION

The present invention relates to a series of new macrolide compounds which are chemically related to certain known classes of macrolides including those known as the milbemycins and the avermectins. These compounds have valuable acaricidal, insecticidal and anthelmintic activities. The invention also provides methods of preparing these compounds and compositions a and methods for using them.

There are several classes of known compounds with structure based on a 16-membered macrolide ring, which compounds are obtained by fermentation of various microorganisms or are obtained semi-synthetically by chemical derivatization of such natural fermentation products, and which exhibit acaricidal, insecticidal, anthelmintic and antiparasitic activities. The milbemycins and avermectins are examples of two such classes of known compounds, but various others also exist and are identified in the art by different names or code numbers. The names for these various macrolide compounds have generally been taken from the names or code numbers of the microorganisms which produce the naturally occurring members of each class, and these names have then been extended to cover the chemical derivatives of the same class, with the result that there has been no standardized systematic nomenclature for such compounds generally.

In order to avoid confusion, a standardized system of nomenclature will be used herein, which follows the normal rules for naming derivatives of organic compounds as recommended by the International Union of Pure and Applied Chemistry (IUPAC), Organic Chemistry Division, Commission on Nomenclature of Organic Chemistry, and which is based primarily on the hypothetical parent compound hereby defined as "milbemycin" and represented by the formula (A):

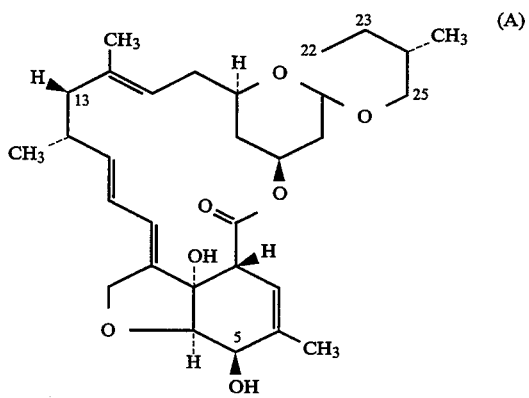

For the avoidance of doubt, formula (A) also shows the numbering of positions of the macrolide ring system applied to those positions most relevant to the compounds of the present invention and of the prior art.

The naturally produced milbemycins are a series of macrolide compounds known to have anthelmintic, acaricidal and insecticidal activities. Milbemycin D was disclosed in U.S. Pat. No. 4,346,171, where it was referred to as "Compound B-41D", and milbemycins $A_3$ and $A_4$ were disclosed in U.S. Pat. No. 3,950,360. These compounds may be represented by the above formula (A) in which there is a hydrogen atom at position 13 and position 25 is substituted with a methyl group, an ethyl group or an isopropyl group, these compounds being designated as milbemycin $A_3$, milbemycin $A_4$ and milbemycin D, respectively. The milbemycin analog having a hydrogen atom at position 13 and substituted at position 25 with a sec-butyl group was disclosed in U.S. Pat. No. 4,173,571, where it was known as "13-deoxy-22,23-dihydroavermectin $B_{1a}$ aglycone". Certain of the compounds of the present invention are named as derivatives of this and related compounds, the numbering system being as shown above on formula (A).

Subsequently, various derivatives of the original milbemycins and avermectins have been prepared and their activities investigated. For example, 5-esterified milbemycins have been disclosed in U.S. Pat. No. 4,201,861, No. 4,206,205, No. 4,173,571, No. 4,171,314, No. 4,203,976, No. 4,289,760, No. 4,457,920, No. 4,579,864 and No. 4,547,491, in European Patent Publications No. 8184, No. 102,721, No. 115,930, No. 180,539 and No. 184,989 and in Japanese Patent Applications Kokai (i.e. as laid open to public inspection) No. 57-120589 and 59-16894.

13-Hydroxy-5-ketomilbemycin derivatives have been disclosed in U.S. Pat. No. 4,423,209. Milbemycin 5-oxime derivatives were disclosed in U.S. Pat. No. 4,547,520 and in European Patent Publication No. 203 832.

Milbemycins having an ether linkage at the 13 position are of particular relevance to the present invention and the lower alkyl, phenyl and benzyl ethers are described in general terms in U.S. Pat. No. 4,696,945, but only the methyl and ethyl ethers are specifically described in the Examples. Certain other milbemycin derivatives having a 13-ether group are disclosed in European Patent Publication No. 357 460.

Like the milbemycins, the avermectins are based upon the same 16-membered ring macrolide compound. The avermectins are disclosed, for example in J. Antimicrob. Agents Chemother., 15(3), 361–367 (1979). These compounds may be represented by the above formula (A) but with a carbon-carbon double bond at positions 22 and 23, and having position 13 substituted with a 4'-(α-L-oleandrosyl)-α-L-oleandrosyloxy group. Position 25 may be substituted with an isopropyl group or a sec-butyl group, these compounds being designated as avermectin $B_{1b}$ and avermectin $B_{1a}$, respectively. 22,23-Dihydroavermectins $B_{1a}$ and $B_{1b}$ may be obtained by reduction of the double bond between the 22 and 23 positions and are disclosed in U.S. Pat. No. 4,199,569. The aglycone derivatives of the avermectins, which are milbemycin analogs, have sometimes been referred to in the literature as C-076 compounds, and various derivatives of these are known. For example, U.S. Pat. No. 4,201,861 discloses such derivatives substituted with a lower alkanoyl group at position 13.

European Patent Publication No. 170 006 discloses a family of bioactive compounds produced by fermentation, identified collectively by the code number LL-F28249. Some of these have a 16-membered macrolide structure corresponding to the above formula (A), substituted with a hydroxy group at position 23 and with a 1-methyl-1-propenyl, 1-methyl-1-butenyl or 1,3-dimethyl-1-butenyl group at position 25. In these compounds, the hydroxy group at position 5 may also be replaced by a methoxy group.

British Patent Publication No. 2,176,182 discloses another group of macrolide antibiotics corresponding to the above formula (A) with a hydroxy or substituted hydroxy group at position 5, a hydroxy, substituted hydroxy or keto group at position 23, and an α-branched alkenyl group at position 25.

The various classes of milbemycin-related macrolide compounds described above are all disclosed as having one or more types of activity as antibiotic, anthelmintic, ectoparasiticidal, acaricidal or other pesticidal agents. However, there is still a continuing need to provide such agents with improved activity against one or more classes of pests.

It has now been discovered that the activity of such milbemycin-related derivatives can be improved by appropriately selecting the combination of substituents on the macrolide ring system, especially the substituents at position 13. In particular, it has now been found that the activity of the compounds can be improved upon by appropriate selection of certain highly specific ether groups at the 13 position, as specified below.

BRIEF SUMMARY OF INVENTION

Accordingly, it is an object of the present invention to provide such macrolide compounds having improved activity. It is another object of the invention to provide methods for preparing such compounds. It is a still further object of the invention to provide pesticidal compositions and methods using the said compounds.

In accordance with these objects, the invention provides compounds having the formula (I):

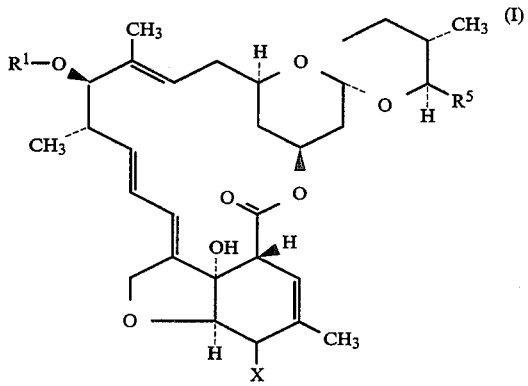

in which:

$R^1$ represents: an alkyl group having from 4 to 8 carbon atoms; a cycloalkyl group having from 4 to 8 carbon atoms; an alkyl group having from 1 to 4 carbon atoms and substituted by a cycloalkyl group having from 3 to 8 carbon atoms, said cycloalkyl group being unsubstituted or having at least one substituent selected from the group consisting of substituents (c); or a group having one of the following formulae:

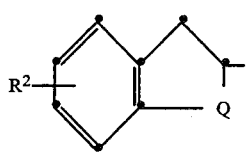

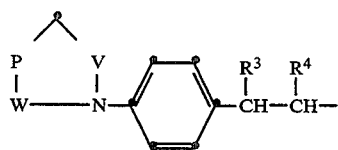

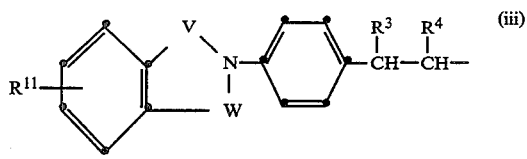

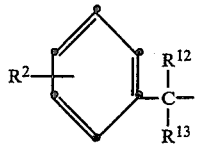

wherein:

$R^2$ represents: a hydrogen atom; a halogen atom; a cyano group; a nitro group; an alkyl group having from 1 to 4 carbon atoms; a substituted alkyl group which has from 1 to 4 carbon atoms and which has at least one substituent selected from the group consisting of substituents (a); an alkoxy group having from 1 to 4 carbon atoms; an alkoxyalkoxy group having a total of from 2 to 6 carbon atoms; or a group having one of the following formulae:

—$(CH_2)_n NHR^9$
—$(CH_2)_n NR^9 COR^6$
—$(CH_2)_n NR^9 COCOR^6$
—$(CH_2)_n NR^9 COCOOR^7$
—$(CH_2)_n NR^9 CHR^6 NHCOR^6$
—$(CH_2)_n NR^9 CHR^6 NHCONHR^6$
—$(CH_2)_n NR^9 CHR^6 NHCOOR^7$
—$(CH_2)_n NR^9 C(=Y)YR^6$
—$(CH_2)_n NR^9 C(=Y)NR^6 R^6$
—$(CH_2)_n NR^9 C(=Y)NR^6 NR^6 R^6$
—$(CH_2)_n NR^9 C(=Y)NR^6 NHZ$
—$(CH_2)_n NR^9 C(=NR^{10})NHR^{10}$
—$(CH_2)_n NR^9 C(=NR^{10})R^6$ or
—$(CH_2)_n NR^9 SO_m R^6$ wherein:

m is 1 or 2;
n is 0, 1 or 2;

$R^6$ represents a hydrogen atom; an alkyl group having from 1 to 8 carbon atoms; a substituted alkyl group having from 1 to 8 carbon atoms and having at least one substituent selected from the group consisting of substituents (b); an aliphatic hydrocarbon group having from 2 to 8 carbon atoms and having one or two carbon-carbon double or triple bonds; a cycloalkyl group having from 3 to 8 carbon atoms; a substituted cycloalkyl group having from 3 to 8 carbon atoms and having at least one substituent selected from the group consisting of substituents (c); an aryl group which has from 6 to 14 ring carbon atoms and which is unsubstituted or which has at least one substituent selected from the group consisting of substituents (c); an aryloxy group which has from 6 to 14 ring carbon atoms and which is unsubstituted or which has at least one substituent selected from the group consisting of substituents (c); an arylthio group which has from 6 to 14 ring carbon atoms and which is unsubstituted or which has at least one substituent selected from the group consisting of substituents (c); or a heterocyclic group having from 3 to 6 ring atoms, of which at least one is a hetero-atom selected from the group consisting of nitrogen, oxygen and sulfur hetero-atoms, said heterocyclic group being unsubstituted or having at least one substituent selected from the group consisting of substituents (c) and being a monocyclic ring or being fused to one or two benzene or monocyclic aromatic heterocylic rings, said monocyclic aromatic heterocyclic ring having 5 or 6 ring atoms of which from 1 to 3 are hetero-atoms selected from the group consisting of nitrogen, oxygen and sulfur hetero-atoms, to form a bicyclic or tricyclic ring system; and, where there are two or more groups or atoms represented by $R^6$, these are the same or different from each other; or, where two groups represented by $R^6$ are attached to a single nitrogen atom, these groups $R^6$, together with a nitrogen atom to which they are attached, may be fused to form a heterocyclic ring having from 3 to 7 ring atoms, which ring additionally contains 0 or 1 further hetero-atom selected from the group consisting of oxygen, nitrogen and sulfur atoms, in addition to said nitrogen atom; or, where two groups represented by $R^6$ are attached to adjacent nitrogen atoms, these groups $R^6$, together with a nitrogen atoms to which they are attached, may be fused to form a heterocyclic ring having from 3 to 7 ring atoms, which ring additionally contains 0 or 1 further hetero-atom selected from the group consisting of oxygen, nitrogen and sulfur atoms, in addition to said nitrogen atoms;

$R^7$ represents an alkyl group having from 1 to 4 carbon atoms, a cycloalkyl group having from 3 to 7 carbon atoms, or an aralkyl group in which an alkyl group having from 1 to 4 carbon atoms is substituted by from 1 to 3 aryl groups which have from 6 to 10 ring carbon atoms and which have at least one substituent selected from the group consisting of substituents (c);

$R^9$ represents a hydrogen atom or an alkyl group having from 1 to 4 carbon atoms;

$R^{10}$ represents any of the groups or atoms defined above for $R^6$, or it represents a cyano group, a nitro group, a group of formula —$COOR^7$ (wherein $R^7$ is as defined above), or a group of formula —$COR^6$ (wherein $R^6$ is as defined above);

Y represents an oxygen atom or a sulfur atom; and, where there are two or more groups represented by Y, these are the same or different from each other;

Z represents a group of formula —$COOR^7$ (wherein $R^7$ is as defined above), a group of formula —$COR^6$ (wherein $R^6$ is as defined above) or a group of formula —$SO_2R^6$ (wherein $R^6$ is as defined above);

Q represents a methylene group, an ethylene group or a group of formula —$OCH_2$—;

P represents a methylene group, an ethylene group, an oxygen atom or a direct carbon-carbon single bond between the group represented by W and the methylene group to which P is shown as attached;

V and W are the same or different from each other and each represents a methylene group, a carbonyl group or a thiocarbonyl group;

$R^3$ and $R^4$ are independently selected from the group consisting of hydrogen atoms, alkyl groups having from 1 to 4 carbon atoms and alkoxy groups having from 1 to 4 carbon atoms;

$R^{11}$ represents an alkyl group having from 1 to 4 carbon atoms, an alkoxy group having from 1 to 4 carbon atoms, an alkylthio group having from 1 to 4 carbon atoms, an alkanoyloxy group having from 1 to 5 carbon atoms, an alkoxycarbonyl group having from 2 to 5 carbon atoms, a halogen atom, a cyano group, a nitro group, an amino group, an alkylamino group in which the alkyl part has from 1 to 4 carbon atoms, a dialkylamino group in which each alkyl part has from 1 to 4 carbon atoms, a carbamoyl group, an alkylcarbamoyl group in which the alkyl part has from 1 to 4 carbon atoms, a dialkylcarbamoyl group in which each alkyl part has from 1 to 4 carbon atoms, or an alkanoylamino group having from 1 to 5 carbon atoms;

$R^{12}$ represents a hydrogen atom or an alkyl group having from 1 to 4 carbon atoms;

$R^{13}$ represents an alkyl group having from 1 to 4 carbon atoms;

$R^5$ represents a methyl group, an ethyl group, an isopropyl group or a sec-butyl group; and X represents: a hydroxy group; an alkanoyloxy group which has from 1 to 5 carbon atoms, and which is unsubstituted or has at least one substituent selected from the group consisting of substituents (d); or a hydroxyimino group;

substituents (a)

halogen atoms, alkoxy groups having from 1 to 4 carbon atoms, alkylthio groups having from 1 to 4 carbon atoms, and alkanoyloxy groups having from 1 to 5 carbon atoms;

substituents (b)

cycloalkyl groups having from 3 to 8 carbon atoms; alkoxy groups having from 1 to 4 carbon atoms; alkylthio groups having from 1 to 4 carbon atoms; cyanoalkylthio groups having from 2 to 5 carbon atoms; alkoxycarbonyl groups having from 2 to 5 carbon atoms; halogen atoms; cyano groups; nitro groups; amino groups; aryl groups which have from 6 to 14 ring carbon atoms and which are unsubstituted or have at least one substituent selected from the group consisting of substituents (c); aromatic heterocyclic groups which have 5 or 6 ring atoms and which are unsubstituted or which have at least one substituent selected from the group consisting of substituents (c) and such heterocyclic groups which are fused to one or two benzene or monocyclic aromatic heterocyclic rings, said monocyclic aromatic heterocyclic ring having 5 or 6 ring atoms of which from 1 to 3 are hetero-atoms selected from the group consisting of nitrogen, oxygen and sulfur hetero-atoms, to form a bicyclic or tricyclic group; aryloxy groups which have from 6 to 14 ring carbon atoms and which are unsubstituted or have at least one substituent selected from the group consisting of substituents (c); and arylthio groups which have from 6 to 14 ring carbon atoms and which are unsubstituted or have at least one substituent selected from the group consisting of substituents (c);

substituents (c)

alkyl groups having from 1 to 4 carbon atoms, alkoxy groups having from 1 to 4 carbon atoms, alkylthio groups having from 1 to 4 carbon atoms, alkanoyloxy groups having from 1 to 5 carbon atoms, alkoxycarbonyl groups having from 2 to 5 carbon atoms, halogen atoms, cyano groups, nitro groups, amino groups, alkylamino groups in which the alkyl part has from 1 to 4 carbon atoms, dialkylamino groups in which each alkyl part is independently selected from the group consisting of alkyl groups having from 1 to 4 carbon atoms, carbamoyl groups, alkylcarbamoyl groups in which the alkyl part has from 1 to 4 carbon atoms, dialkylcarbamoyl groups in which each alkyl part is independently selected from the group consisting of alkyl groups having from 1 to 4 carbon atoms, and alkanoylamino groups having from 1 to 5 carbon atoms;

substituents (d)

halogen atoms, alkoxy groups having from 1 to 4 carbon atoms, alkoxycarbonyl groups having from 2 to 5 carbon atoms, and carboxy groups; and salts and esters thereof.

The invention still further provides an anthelmintic, acaricidal and insecticidal composition comprising an anthelmintic, acaricidal and insecticidal compound in admixture with a pharmaceutically, agriculturally, veterinarily or horticulturally acceptable carrier or diluent, wherein said compound is selected from the group consisting of compounds of formula (I) and salts and esters thereof.

The invention still further provides a method of treating an animal, which may be human or non-human, parasitized by a parasite selected from the group consisting of helminths, acarids and insects by administering thereto at least one compound selected from the group consisting of compounds of formula (I) and salts and esters thereof.

The invention still further provides a method of protecting animals or plants from damage by parasites selected from the group consisting of acarids, helminths and insects, which comprises applying an active compound to said animals, to said plants or to seeds of said plants or to a locus including said animals, plants or seeds, wherein the active compound is selected from the group consisting of at least one compound of formula (I) and salts and esters thereof.

DETAILED DESCRIPTION OF INVENTION

In the compounds of the present invention, when $R^1$ represents an alkyl group having from 4 to 8 carbon atoms, this may be a straight or branched chain group, preferably a branched chain group, having from 4 to 8, preferably from 4 to 6, carbon atoms, and examples include the butyl, isobutyl, sec-butyl, t-butyl, pentyl, isopentyl, hexyl, 1,3-dimethylbutyl, heptyl, octyl, 1-methylheptyl and 2-ethylhexyl groups. Of these, the butyl, isobutyl, sec-butyl and t-butyl groups are more preferred and the t-butyl group is most preferred.

When $R^1$ represents a cycloalkyl group, this has from 4 to 8 carbon atoms, and examples include the cyclobutyl, cyclopentyl, cyclohexyl, cycloheptyl and cyclooctyl groups.

Where $R^2$ represents a halogen atom, this may be a fluorine, chlorine, bromine or iodine atom, preferably a chlorine or bromine atom.

When $R^2$ represents an alkyl group, this may be a straight or branched chain alkyl group having from 1 to 4 carbon atoms, and examples include the methyl, ethyl, propyl, isopropyl, butyl, isobutyl, sec-butyl and t-butyl groups, of which we prefer the methyl, ethyl, propyl, isopropyl, butyl and sec-butyl groups, most preferably the methyl group or the ethyl group. Such groups may be unsubstituted or they may have at least one substituent selected from the group consisting of substituents (a), defined above and exemplified below. Where the group is substituted, there is no particular restriction on the number of substituents, except such as may be imposed by the number of substitutable positions, and, possibly, by steric constraints. Examples of groups and atoms which may be represented by substituents (a) include:

halogen atoms, such as the fluorine, chlorine, bromine and iodine atoms;

alkoxy groups having from 1 to 4 carbon atoms, which may be straight or branched chain alkoxy groups having from 1 to 4 carbon atoms, and examples include the methoxy, ethoxy, propoxy, isopropoxy, butoxy, isobutoxy, sec-butoxy and t-butoxy groups, of which we prefer the methoxy, ethoxy, propoxy, isopropoxy and butoxy groups, most preferably the methoxy group;

alkylthio groups having from 1 to 4 carbon atoms, which may be straight or branched chain alkylthio groups having from 1 to 4 carbon atoms, and examples include the methylthio, ethylthio, propylthio, isopropylthio, butylthio, isobutylthio, sec-butylthio and t-butylthio groups, of which we prefer the methylthio, ethylthio, propylthio, isopropylthio, butylthio and isobutylthio groups, most preferably the methylthio group; and alkanoyloxy groups having from 1 to 5 carbon atoms, which may be straight or branched chain groups, such as the formyloxy, acetoxy, propionyloxy, butyryloxy, isobutyryloxy, valeryloxy, isovaleryloxy and pivaloyloxy groups, of which we prefer the formyloxy, propionyloxy, butyryloxy, isovaleryloxy and pivaloyloxy groups.

When $R^2$ represents an alkoxy group, this may be a straight or branched chain alkoxy group having from 1 to 4 carbon atoms, and examples include the methoxy, ethoxy, propoxy, isopropoxy, butoxy, isobutoxy, sec-butoxy and t-butoxy groups, of which we prefer the methoxy, ethoxy, propoxy, isopropoxy, butoxy and sec-butoxy groups, most preferably the methoxy group.

Where $R^2$ represents an alkoxyalkoxy group, this has a total of from 2 to 6 carbon atoms, and each alkoxy part may be a straight or branched chain group, although each is preferably straight chain; preferably each alkoxy part has from 1 to 4 carbon atoms, provided that they total no more than 6. Examples of such groups include the methoxymethoxy, ethoxymethoxy, propoxymethoxy, butoxymethoxy, methoxyethoxy, ethoxyethoxy and butoxyethoxy groups.

Where $R^6$ represents an alkyl group this may be a straight or branched chain alkyl group having from 1 to 8, preferably from 1 to 4, carbon atoms, and the group may be unsubstituted or it may be substituted by at least one of substituents (b), defined above and exemplified below. Examples of such alkyl groups include the methyl, ethyl, propyl, isopropyl, butyl, isobutyl, sec-butyl, t-butyl, pentyl, isopentyl, neopentyl, hexyl, isohexyl, sec-hexyl, t-hexyl, heptyl, isoheptyl and octyl groups, preferably the methyl, ethyl, propyl, isopropyl, butyl, sec-butyl, pentyl, isopentyl, hexyl, sec-hexyl and heptyl groups. Examples of the groups and atoms which may be included in substituents (b) include:

cycloalkyl groups having from 3 to 8 carbon atoms, such as the cyclopropyl, cyclobutyl, cyclopentyl, cyclohexyl and cycloheptyl groups;

halogen atoms, alkoxy groups having from 1 to 4 carbon atoms and alkylthio groups having from 1 to 4 carbon atoms, such as those exemplified in relation to substituents (a);

cyanoalkylthio groups having from 2 to 5 carbon atoms, such as the cyanomethylthio, 1-cyanoethylthio, 2-cyanoethylthio, 1-cyanopropylthio, 2-cyanopropylthio and 1-cyanobutylthio groups;

alkoxycarbonyl groups having from 2 to 5 carbon atoms such as the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups, preferably the methoxycarbonyl, ethoxycarbonyl, propoxycarbonyl and butoxycarbonyl groups;

cyano groups, nitro groups and amino groups;

carbocyclic aryl groups which have from 6 to 14, preferably from 6 to 10 and more preferably 6 or 10, ring carbon atoms and which are unsubstituted or have at least one substituent selected from the group consisting of substituents (c), defined and exemplified below, such as the phenyl, naphthyl (1- or 2-) and anthryl groups, of which the phenyl and naphthyl groups are preferred and the phenyl group is most preferred; such groups may be unsubstituted or substituted;

aromatic heterocyclic groups which have 5 or 6 ring atoms and which are unsubstituted or which have at least one substituent selected from the group consisting of substituents (c); examples of the unsubstituted groups include the pyridyl, thienyl, furyl, pyrrolyl, imidazolyl, triazolyl, tetrazolyl, thiazolyl and oxazolyl groups, and such groups which are fused to at least one benzene ring, such as the indolyl group; any of these groups may be unsubstituted or they may be substituted by at least one of substituents (c), defined above and exemplified below;

aryloxy groups which have from 6 to 14 ring carbon atoms and which are unsubstituted or have at least one substituent selected from the group consisting of substituents (c); and arylthio groups which have from 6 to 14 ring carbon atoms and which are unsubstituted or have at least one substituent selected from the group consisting of substituents (c); in each case, the aryl part of these groups may be as exemplified above in relation to the aryl groups.

Examples of the groups and atoms which may be represented by substituents (c) include:

alkyl groups having from 1 to 4 carbon atoms, alkoxy groups having from 1 to 4 carbon atoms, alkylthio groups having from 1 to 4 carbon atoms, alkanoyloxy groups having from 1 to 5 carbon atoms, alkoxycarbonyl groups having from 2 to 5 carbon atoms and halogen atoms, such as those exemplified above in relation to substituents (a) and/or (b);

cyano groups, nitro groups and amino groups;

alkylamino groups and dialkylamino groups in which the or each alkyl part has from 1 to 4 carbon atoms, such as the methylamino, ethylamino, propylamino, isopropylamino, dimethylamino, diethylamino, N-butyl-N-methylamino, N-t-butyl-N-methylamino, N-methyl-N-propylamino, N-ethyl-N-propylamino, dipropylamino, diisopropylamino, butylamino, isobutylamino, dibutylamino and diisobutylamino groups, especially the methylamino, ethylamino, propylamino, butylamino, dimethylamino and diethylamino groups;

carbamoyl groups, alkylcarbamoyl groups and dialkylcarbamoyl groups in which the or each alkyl part is independently selected from the group consisting of alkyl groups having from 1 to 4 carbon atoms, such as the carbamoyl, methylcarbamoyl, ethylcarbamoyl, propylcarbamoyl, isopropylcarbamoyl, dimethylcarbamoyl, diethylcarbamoyl, N-butyl-N-methylcarbamoyl, N-t-butyl-N-methylcarbamoyl, N-methyl-N-propylcarbamoyl, N-ethyl-N-propylcarbamoyl, dipropylcarbamoyl, diisopropylcarbamoyl, butylcarbamoyl, isobutylcarbamoyl, dibutylcarbamoyl and diisobutylcarbamoyl groups, especially the methylcarbamoyl, ethylcarbamoyl, propylcarbamoyl, butylcarbamoyl, dimethylcarbamoyl and diethylcarbamoyl groups; and alkanoylamino groups having from 1 to 5 carbon atoms, which may be straight or branched chain groups, such as the formamido, acetamido, propionamido, butyramido, isobutyramido, valeramido, isovaleramido and pivaloylamino groups, of which we prefer the formamido, acetamido, propionamido and butyramido groups.

Where $R^6$ represents an aliphatic hydrocarbon group having one or two carbon-carbon double or triple bonds, this is preferably an alkenyl group, an alkadienyl group or an alkynyl group, and may be a straight or branched chain group having from 2 to 8, preferably from 2 to 6, and more preferably 3 or 4, carbon atoms. Examples of the alkenyl groups include the vinyl, allyl, methallyl, 1-propenyl, isopropenyl, 1-butenyl, 2-butenyl, 3-butenyl, 1-pentenyl, 2-pentenyl, 3-pentenyl and 4-pentenyl groups, of which the allyl, methallyl, 1-propenyl, isopropenyl and butenyl groups are preferred, the allyl and 2-butenyl groups being most preferred. Examples of the alkadienyl groups include groups having from 3, preferably from 4, to 8 carbon atoms, such as the butadienyl and hexadienyl groups, more preferably the hexadienyl group. Examples of the alkynyl groups include the ethynyl, propargyl (2-propynyl), 1-propynyl, 1-butynyl, 2-butynyl, 3-butynyl, 1-pentynyl, 2-pentynyl, 3-pentynyl and 4-pentynyl groups, of which the propynyl and butynyl groups are preferred, the propargyl and 2-butynyl groups being most preferred.

Where $R^6$ represents a cycloalkyl group, this has from 3 to 8 carbon atoms, and examples include the cyclopropyl, cyclobutyl, cyclopentyl, cyclohexyl, cycloheptyl and cyclooctyl groups, and it may be unsubstituted or it may have at least one substituent selected from the group consisting of substituents (c), defined and exemplified above.

Where $R^6$ represents an aryl, aryloxy or arylthio group, this may be as exemplified above in relation to substituents (b).

Where $R^6$ represents a heterocyclic group, this may be a saturated or unsaturated group containing from 3 to 6 ring atoms, of which at least one, and preferably from 1 to 3, is a nitrogen, oxygen or sulfur atom. More preferably the group has from 0 to 3 such nitrogen atoms, 0, 1 or 2 such oxygen atoms and 0, 1 or 2 such sulfur atoms, provided that the total number of heteroatoms is not less than 1 and does not exceed 3. More preferably, where the group has two or three heteroatoms, at least one of these is a nitrogen atom, and the remaining one or two are selected from nitrogen, oxygen and sulfur hetero-atoms. Where the group is unsaturated, it may be non-aromatic or aromatic in character. The group may be monocyclic or it may be fused to one or two benzene rings to produce a bicyclic or tricyclic group, in which the heterocyclic part may be aromatic or non-aromatic in character. Examples of such groups include the oxiranyl, oxetanyl, aziridinyl, azetidinyl, thiranyl, thietanyl, furyl, thienyl, pyrrolyl, pyridyl, thiazolyl, isothiazolyl, oxazolyl, isoxazolyl, imidazolyl, pyrazolyl, pyranyl, pyrazinyl, pyridazinyl, pyrimidinyl, benzofuranyl, isobenzofuranyl, benzothienyl, isobenzothienyl, indolyl, quinolyl, isoquinolyl, quinazolinyl, quinoxalinyl, naphthyridynyl, xanthenyl, tetrahydrofuranyl, tetrahydrothienyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, morpholinyl, thiomorpholinyl, indolinyl, tetrahydroquinolyl, pyrrolidonyl, piperidonyl, pyridonyl, thianthrenyl, chromenyl, phenoxathiinyl, 2H-pyrrolyl, isoindolyl, 3H-indolyl, indazolyl, phthalazinyl, quinoxalinyl, quinazolinyl, cinnolinyl, carbazolyl, phenanthridinyl, acridinyl, perimidinyl, phenazinylphenothiazinyl, furazanyl, phenoxazinyl, isochromanyl, chromanyl, pyrazolinyl, indolinyl and isoindolinyl groups. Such groups may be unsubstituted or they may have at least one substituent selected from the group consisting of substituents (c), defined and exemplified above.

Where $R^2$ represents a group of formula

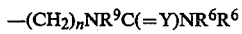
—$(CH_2)_n NR^9 C(=Y)NR^6 R^6$ the two groups $R^6$ attached to a single nitrogen atom may be the same or different and may be selected from those groups represented by $R^6$ and defined and exemplified above. Alternatively, the two groups $R^6$, together with the nitrogen atom to which they are attached, may form a nitrogen-containing heterocyclic group, which may optionally have an additional nitrogen, oxygen or sulfur hetero-atom; such a group may contain from 3 to 7 atoms in total (i.e. including the afore-mentioned nitrogen atom) and may be saturated or unsaturated. If it is unsaturated the unsaturation may be aromatic or non-aromatic in character, provided that the group has a nitrogen atom which can provide the nitrogen atom of the group —$NR^6R^6$. Examples of such groups include the aziridinyl, azetidinyl, pyrrolyl, imidazolyl, pyrazolyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, pyrrolidonyl, piperidonyl, pyridonyl, pyrazolinyl, azepinyl, perhydroazepinyl, oxazepinyl and thiazepinyl groups. Such groups may be unsubstituted or they may have at least one substituent selected from the group consisting of substituents (c), defined and exemplified above.

Where $R^2$ represents a group of formula

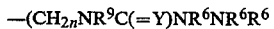
—$(CH_{2n}NR^9C(=Y)NR^6NR^6R^6$ the two groups $R^6$ attached to a single nitrogen atom may be the same or different and may be selected from those groups represented by $R^6$ and defined and exemplified above. Alternatively, the two groups $R^6$, together with the nitrogen atom to which they are attached, may form a nitrogen-containing heterocyclic group, which may optionally have an additional nitrogen, oxygen or sulfur hetero-atom; such a group may contain from 3 to 7 atoms in total (i.e. including the afore-mentioned nitrogen atom) and may be saturated or unsaturated, as defined and exemplified in the preceding paragraph. Alternatively, two of the symbols $R^6$ attached to different nitrogen atoms may form a heterocyclic ring containing at least two nitrogen atoms and optionally another hetero-atom selected from the group consisting of nitrogen, oxygen and sulfur hetero-atoms. Examples of such groups include the divalent groups derived by removal of a hydrogen atom from each of the two adjacent nitrogen atoms of the ring systems: diaziridine, diazete, diazetidine, pyrazolidine, pyrazoline, 1,2-dihydropyridazine, 1,2,3,4-tetrahydropyridazine, 1,2,5,6-tetrahydropyridazine, perhydropyridazine, 1,2-dihydro-1,2-diazepine and perhydro-1,2-diazepine.

Where $R^7$ represents an alkyl group having from 1 to 4 carbon atoms, this may be as defined and exemplified above in relation to the groups which may be represented by $R^1$.

Where $R^7$ represents an aralkyl group, the alkyl part has from 1 to 4 carbon atoms and may be any of the alkyl groups exemplified above, but it is preferably an alkyl group having from 1 to 3 carbon atoms and is more preferably a methyl or ethyl group. The aryl part or parts has or have from 6 to 10 carbon atoms in its ring and again, may be any of the aryl groups exemplified above. There may be from 1 to 3 such aryl groups. Examples of such aralkyl groups include the benzyl, phenethyl, α-methylbenzyl, 1-phenylpropyl, 2-phenylpropyl, 3-phenylpropyl, 4-phenylbutyl, benzhydryl and trityl groups, of which the benzyl and phenethyl groups are preferred.

Where X represents an alkanoyloxy group, it contains from 1 to 5 carbon atoms and may be a straight or branched chain group. Examples of such groups include the formyloxy, acetoxy, propionyloxy, butyryloxy, isobutyryloxy, valeryloxy, isovaleryloxy and pivaloyloxy groups. Such groups may be unsubstituted, or they may have at least one substituent selected from the group consisting of substituents (d), defined above and exemplified below.

Examples of groups and atoms which may be represented by substituents (d) include:

halogen atoms and alkoxy groups having from 1 to 4 carbon atoms, as exemplified in relation to substituents (a);

alkoxycarbonyl groups having from 2 to 5 carbon atoms, as exemplified in relation to substituents (b); and carboxy groups.

In general, in the discussion above, where reference is made to a substituted group, there is no particular restriction on the number of substituents, except such as may be imposed by the number of substitutable positions, or possibly by steric constraints, each of which is well recognised by those skilled in the art. However, as a general rule, we normally find it convenient to have no more than 3 such substituents, and sometimes fewer, i.e. 1, 2 or 3. More preferably, the number of the substituents is 1, 2 or 3 where the substituent is a halogen atom, and 1 in other cases.

Where $R^7$ represents a hydrogen atom or substituent (d) is a carboxy group, the compounds can form salts with various sorts of bases. Such salts include, for example: salts with an alkali metal, such as lithium, sodium or potassium; salts with an alkaline earth metal, such as calcium or barium; salts with another metal, such as magnesium or aluminum; and salts with an organic amine, such as triethylamine or triethanolamine.

Of the compounds of formula (I) of the present invention, representative preferred classes are as follows:

(1) those wherein $R^1$ represents an alkyl group having from 4 to 6 carbon atoms, such as the butyl, isobutyl, sec-butyl, t-butyl, pentyl, isopentyl, neopentyl, t-pentyl, 1-methylbutyl and hexyl groups; a cycloalkyl group having from 4 to 8 carbon atoms, said group being unsubstituted or being substituted by at least one alkyl group having from 1 to 4 carbon atoms, such as the cyclobutyl, cyclopentyl, 1-methylcyclopentyl, cyclohexyl and 1-methylcyclohexyl groups; an alkyl group having from 1 to 4 carbon atoms and substituted by a cycloalkyl group having from 3 to 8 carbon atoms, such as the cyclopentylmethyl, cyclopentylethyl, cyclohexylmethyl, cyclohexylethyl groups;

(2) those wherein $R^1$ represents a group of formula:

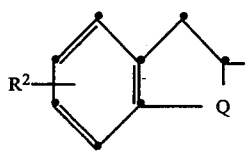 (i)

wherein R² represents a hydrogen atom or a group of formula —NR⁹ᵃCOR⁶ᵃ
wherein:

R⁹ᵃ represents a hydrogen atom or a methyl group;

R⁶ᵃ represents: a hydrogen atom; an alkyl group having from 1 to 4 carbon atoms, such as the methyl, ethyl, propyl, isopropyl and butyl groups; a cycloalkyl group having from 3 to 5 carbon atoms, such as the cyclopropyl, cyclobutyl and cyclopentyl groups; an alkyl group having from 1 to 3 carbon atoms and substituted with a halogen atom, a cyano group, an alkoxy group having from 1 to 3 carbon atoms, an alkylthio group having from 1 to 3 carbon atoms, a cyanomethylthio group or a phenoxy group, such as the fluoromethyl, bromoethyl, difluoromethyl, cyanomethyl, cyanopropyl, methoxymethyl, ethoxymethyl, methylthiomethyl, cyanomethylthiomethyl and phenoxymethyl groups; an alkenyl group, such as the vinyl and allyl groups; a phenyl group; a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; a pyridyl group; a pyrimidyl group; a pyrazinyl group; a furyl group; or a thienyl group; and Q represents a methylene group or an ethylene group;

(3) those wherein R¹ represents a group of formula:

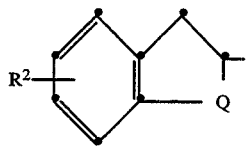 (i)

wherein R² represents a group of formula:

R⁶ᵇ—CO—CO—N(R⁹ᵃ)— wherein:

R⁹ᵃ represents a hydrogen atom or a methyl group; and

R⁶ᵇ represents an alkyl group having from 1 to 4 carbon atoms, such as the methyl, ethyl, propyl, isopropyl and butyl groups; a cycloalkyl group having from 3 to 5 carbon atoms, such as the cyclopropyl, cyclobutyl and cyclopentyl groups; an alkenyl group having from 2 to 4 carbon atoms, such as the vinyl and allyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups;

(4) those wherein R¹ represents a group of formula:

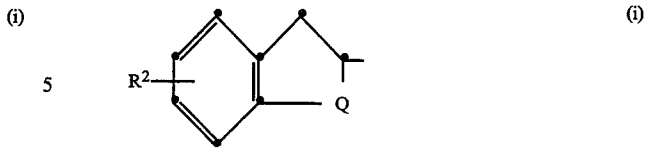 (i)

wherein R² represents a group of formula:

R⁶ᶜ—Y—CY—N(R⁹ᵃ)— wherein

R⁹ᵃ represents a hydrogen atom or a methyl group;

Y represents an oxygen atom; and

R⁶ᶜ represents: an alkyl group having from 1 to 4 carbon atoms, such as the methyl, ethyl, propyl, isopropyl and butyl groups; an alkyl group having from 1 to 4 carbon atoms and substituted with a halogen atom or an alkoxy group having from 1 to 3 carbon atoms, such as the fluoroethyl, trichloroethyl, methoxyethyl and ethoxyethyl groups; a vinyl group; an allyl group; a benzyl group; a methoxybenzyl group; or a nitrobenzyl group;

(5) those wherein R¹ represents a group of formula:

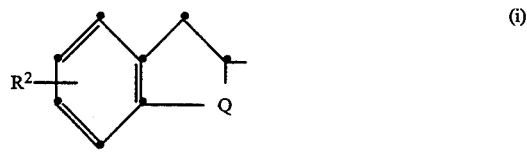 (i)

wherein R² represents a group of formula:

R⁶ᵈN(R⁶ᵉ)—CY—N(R⁹ᵃ)— wherein

R⁹ᵃ represents a hydrogen atom or a methyl group;

Y represents an oxygen atom or a sulfur atom; and

R⁶ᵈ and R⁶ᵉ are the same or different and each represents: a hydrogen atom; an alkyl group having from 1 to 4 carbon atoms, such as the methyl, ethyl, propyl, isopropyl and butyl groups; a cycloalkyl group having from 3 to 6 carbon atoms, such as the cyclopropyl, cyclobutyl, cyclopentyl and cyclohexyl groups; a phenyl group; a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; or R⁶ᵈ and R⁶ᵉ, together with the nitrogen atom to which they are attached, form a piperidine, piperazine, morpholine, pyrrolidine, triazopyridine or aziridine ring;

(6) those wherein R¹ represents a group of formula:

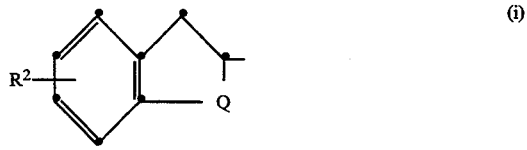 (i)

wherein R² represents a group of formula:

R⁶ʰN(R⁶ᵍ)N(R⁶ᶠ)—CY—N(R⁹ᵃ)— wherein:

$R^{9a}$ represents a hydrogen atom or a methyl group;

Y represents an oxygen atom; and $R^{6f}$, $R^{6g}$ and $R^{6h}$ are the same or different and each represents: a hydrogen atom; an alkyl group having from 1 to 4 carbon atoms, such as the methyl, ethyl, propyl, isopropyl and butyl groups; a cycloalkyl group having from 3 to 6 carbon atoms, such as the cyclopropyl, cyclobutyl, cyclopentyl and cyclohexyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; or $R^{6g}$ and $R^{6h}$, together with the nitrogen atom to which they are attached, form a piperidine, piperazine, morpholine, pyrrolidine or aziridine ring; or $R^{6f}$ and $R^{6g}$, together with the nitrogen atom to which they are attached, form a pyrazolidine or tetrahydropyridazine ring;

(7) those wherein $R^1$ represents a group of formula:

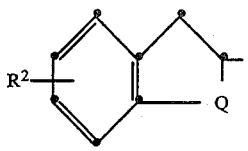

(i)

wherein $R^2$ represents a group of formula:

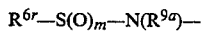

$R^{6r}$—S(O)$_m$—N(R$^{9a}$)— wherein:

$R^{9a}$ represents a hydrogen atom or a methyl group;

m is 1 or 2; and $R^{6r}$ represents an alkyl group having from 1 to 4 carbon atoms, such as the methyl, ethyl, propyl, isopropyl and butyl groups; an alkyl group having from 1 to 3 carbon atoms group and substituted with a cyano group, such as cyanomethyl and cyanoethyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups;

(8) those wherein $R^1$ represents a group of formula:

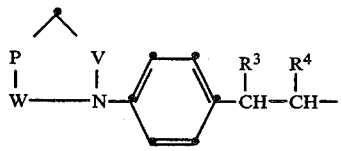

(ii)

wherein:

$R^3$ and $R^4$ are the same or different and each represents a hydrogen atom or a methyl group;

P represents a methylene group, an ethylene group, an oxygen atom or a direct carbon-carbon single bond; and V and W are the same or different and each represents a methylene group or a carbonyl group;

(9) those wherein $R^1$ represents a group of formula:

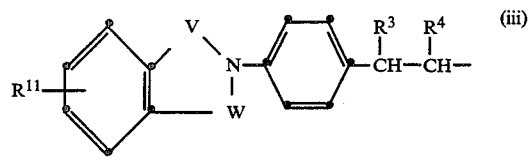

(iii)

wherein:

$R^3$ and $R^4$ are the same or different and each represents a hydrogen atom or a methyl group;

$R^{11}$ represents a hydrogen atom, a methyl group, a fluorine atom or a chlorine atom; and V and W are the same or different and each represents a methylene group or a carbonyl group;

(10) those wherein $R^1$ represents a group of formula:

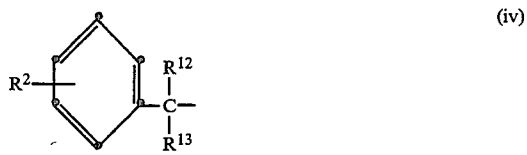

(iv)

wherein:

$R^{12}$ represents a hydrogen atom or an alkyl group having from 1 to 4 carbon atoms;

$R^{13}$ represents an alkyl group having from 1 to 4 carbon atoms; and $R^2$ represents a hydrogen atom or a group of formula —NR$^{9a}$COR$^{6a}$ wherein $R^{6a}$ represents: a hydrogen atom; an alkyl group having from 1 to 4 carbon atoms, such as the methyl, ethyl, propyl, isopropyl and butyl groups; a cycloalkyl group having from 3 to 5 carbon atoms, such as the cyclopropyl, cyclobutyl and cyclopentyl groups; an alkyl group having from 1 to 3 carbon atoms and substituted with a halogen atom, a cyano group, an alkoxy group having from 1 to 3 carbon atoms, an alkylthio group having from 1 to 3 carbon atoms, a cyanomethylthio group or a phenoxy group, such as the fluoromethyl, bromoethyl, difluoromethyl, cyanomethyl, cyanopropyl, methoxymethyl, ethoxymethyl, methylthiomethyl, cyanomethylthiomethyl and phenoxymethyl groups; an alkenyl group having from 2 to 4 carbon atoms, such as the vinyl and allyl groups; a phenyl group; a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; a pyridyl group; a pyrimidyl group; a pyrazinyl group; a furyl group; or a thienyl group;

(11) those wherein $R^1$ represents a group of formula:

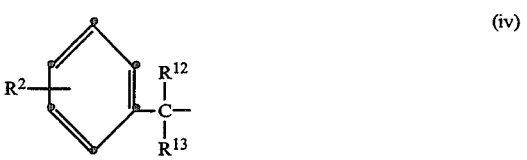

(iv)

wherein:

$R^{12}$ represents a hydrogen atom or an alkyl group having from 1 to 4 carbon atoms;

$R^{13}$ represents an alkyl group having from 1 to 4 carbon atoms; and $R^2$ represents a group of formula $R^{6b}$—CO—CO—N($R^{9a}$)—
wherein:

$R^{9a}$ represents a hydrogen atom or a methyl group; and $R^{6b}$ represents an alkyl group having from 1 to 4 carbon atoms, such as the methyl, ethyl, propyl, isopropyl and butyl groups; a cycloalkyl group having from 3 to 5 carbon atoms, such as the cyclopropyl, cyclobutyl and cyclopentyl groups; an alkenyl group having from 2 to 4 carbon atoms, such as the vinyl and allyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups;

(12) those wherein $R^1$ represents a group of formula:

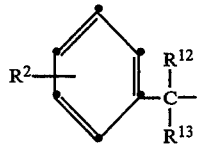

(iv)

wherein:

$R^{12}$ represents a hydrogen atom or an alkyl group having from 1 to 4 carbon atoms;

$R^{13}$ represents an alkyl group having from 1 to 4 carbon atoms; and $R^2$ represents a group of formula $R^{6c}$—Y—CY—N($R^{9a}$)—
wherein:

$R^{9a}$ represents a hydrogen atom or a methyl group;

Y represents an oxygen atom; and $R^{6c}$ represents: an alkyl group having from 1 to 4 carbon atoms, such as the methyl, ethyl, propyl, isopropyl and butyl groups; an alkyl group having from 1 to 4 carbon atoms and substituted with a halogen atom or an alkoxy group having from 1 to 3 carbon atoms, such as the fluoroethyl, trichloroethyl, methoxyethyl and ethoxyethyl groups; a vinyl group; an allyl group; a benzyl group; a methoxybenzyl group; or a nitrobenzyl group;

(13) those wherein $R^1$ represents a group of formula:

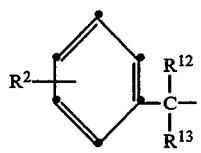

(iv)

wherein:

$R^{12}$ represents a hydrogen atom or an alkyl group having from 1 to 4 carbon atoms;

$R^{13}$ represents an alkyl group having from 1 to 4 carbon atoms; and $R^2$ represents a group of formula $R^{6d}$N($R^{6e}$)—CY—N($R^{9a}$)— wherein:

$R^{9a}$ represents a hydrogen atom or a methyl group;

Y represents an oxygen atom or a sulfur atom; and $R^{6d}$ and $R^{6e}$ are the same or different and each represents: a hydrogen atom; an alkyl group having from 1 to 4 carbon atoms, such as the methyl, ethyl, propyl, isopropyl and butyl groups; a cycloalkyl group having from 3 to 6 carbon atoms, such as the cyclopropyl, cyclobutyl, cyclopentyl and cyclohexyl groups; a phenyl group; a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; or $R^{6d}$ and $R^{6e}$, together with the nitrogen atom to which they are attached, form a piperidine, piperazine, morpholine, pyrrolidine, triazopyridine or aziridine ring;

(14) those wherein $R^1$ represents a group of formula:

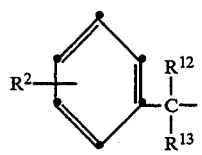

(iv)

wherein:

$R^{12}$ represents a hydrogen atom or an alkyl group having from 1 to 4 carbon atoms;

$R^{13}$ represents an alkyl group having from 1 to 4 carbon atoms; and $R^2$ represents a group of formula $R^{6h}$N($R^{6g}$)N($R^{6f}$)—CY—N($R^{9a}$)— wherein:

$R^{9a}$ represents a hydrogen atom or a methyl group;

Y represents an oxygen atom; and $R^{6f}$, $R^{6g}$ and $R^{6h}$ are the same or different and each represents: a hydrogen atom; an alkyl group having from 1 to 4 carbon atoms, such as the methyl, ethyl, propyl, isopropyl and butyl groups; a cycloalkyl group having from 3 to 6 carbon atoms, such as the cyclopropyl, cyclobutyl, cyclopentyl and cyclohexyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups; or $R^{6g}$ and $R^{6h}$, together with the nitrogen atom to which they are attached, form a piperidine, piperazine, morpholine, pyrrolidine or aziridine ring; or $R^{6f}$ and $R^{6g}$, together with the nitrogen atom to which they are attached, form a pyrazolidine or tetrahydropyridazine ring;

(15) those wherein $R^1$ represents a group of formula:

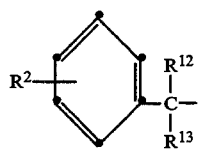

(iv)

wherein:

$R^{12}$ represents a hydrogen atom or an alkyl group having from 1 to 4 carbon atoms;

$R^{13}$ represents an alkyl group having from 1 to 4 carbon atoms; and $R^2$ represents a group of formula $R^{6r}$—S(O)$_m$—N($R^{9a}$)— wherein:

$R^{9a}$ represents a hydrogen atom or a methyl group;

m is 1 or 2; and $R^{6r}$ represents an alkyl group having from 1 to 4 carbon atoms, such as the methyl, ethyl, propyl, isopropyl and butyl groups; an alkyl group having from 1 to 3 carbon atoms group and substituted with a cyano group, such as cyanomethyl and cyanoethyl groups; a phenyl group; or a phenyl group substituted with an alkyl group having from 1 to 3 carbon atoms, an alkoxy group having from 1 to 3 carbon atoms, a halogen atom or a nitro group, such as the tolyl, methoxyphenyl, fluorophenyl and nitrophenyl groups;

(16) compounds as defined in any one of (1) to (15) above, wherein $R^5$ represents an ethyl group; and

(17) compounds as defined in (16) above, wherein X represents a hydroxy group.

Typical examples of compounds of the present invention are as follows:

13-Butoxymilbemycin $A_4$,
13-Isobutoxymilbemycin $A_4$,
13-sec-Butoxymilbemycin $A_4$,
13-t-Butoxymilbemycin $A_4$,
13-(1,1-Dimethylpropoxy)milbemycin $A_4$,
13-(1,2-Dimethylpropoxy)milbemycin $A_4$,
13-(1,2,2-Trimethylpropoxy)milbemycin $A_4$,
13-(3,3-Dimethylbutoxy)milbemycin $A_4$,
13-Pentyloxymilbemycin $A_4$,
13-Isopentyloxymilbemycin $A_4$,
13-Neopentyloxymilbemycin $A_4$,
13-Neopentyloxymilbemycin $A_3$,
13-Neopentyloxymilbemycin D,
13-Deoxy-13-neopentyloxy-22,23-dihydroavermectin $B_{1a}$ aglycone
13-t-Pentyloxymilbemycin $A_4$,
13-Hexyloxymilbemycin $A_4$,
13-Cyclobutyloxymilbemycin $A_4$,
13-Cyclobutylmethoxymilbemycin $A_4$,
13-Cyclopentyloxymilbemycin $A_4$,
13-Cyclopentylmethoxymilbemycin $A_4$,
13-Cyclopentylethoxymilbemycin $A_4$,
13-Cyclohexyloxymilbemycin $A_4$,
13-Cyclohexylmethoxymilbemycin $A_4$,
13-Cyclohexylethoxymilbemycin $A_4$,
13-Cyclohexylethoxymilbemycin $A_3$,
13-Cyclopentyloxymilbemycin D,
13-Deoxy-13-cyclopentyloxy-22,23-dihydroavermectin $B_{1a}$ aglycone
13-(2-Indanyloxy)milbemycin $A_4$,
13-(5-Nitro-2-indanyloxy)milbemycin $A_4$,
13-(5-Amino-2-indanyloxy)milbemycin $A_4$,
13-(5-Acetamido-2-indanyloxy)milbemycin $A_4$,
13-(5-Cyanoacetamido-2-indanyloxy)milbemycin $A_4$,
13-(5-Cyanoacetamido-2-indanyloxy)milbemycin $A_3$,
13-(5-Cyanoacetamido-2-indanyloxy)milbemycin D,
13-Deoxy-13-(5-cyanoacetamido-2-indanyloxy)-22,23-dihydroavermectin $B_{1a}$ aglycone,
13-[5-(N-Cyanoacetyl)methylamino-2-indanyloxy]milbemycin $A_4$,
13-(5-Methoxyacetamido-2-indanyloxy)milbemycin $A_4$,
13-(5-Fluoroacetamido-2-indanyloxy)milbemycin $A_4$,
13-(5-Difluoroacetamido-2-indanyloxy)milbemycin $A_4$,
13-(5-Methoxycarbonylamino-2-indanyloxy)milbemycin $A_4$,
13-(5-Methoxycarbonylamino-2-indanyloxy)milbemycin $A_3$,
13-(5-Methoxycarbonylamino-2-indanyloxy)milbemycin D
13-Deoxy-13-(5-methoxycarbonylamino-2-indanyloxy)-22,23-dihydroavermectin $B_{1a}$ aglycone,
13-[5-(N-Methoxycarbonyl)methylamino-2-indanyloxy]milbemycin $A_4$,
13-(5-Ethoxycarbonylamino-2-indanyloxy)milbemycin $A_4$,
13-(5-Ethoxycarbonylamino-2-indanyloxy)milbemycin $A_3$,
13-(5-Ethoxycarbonylamino-2-indanyloxy)milbemycin D,
13-Deoxy-13-(5-ethoxycarbonylamino-2-indanyloxy)-22,23-dihydroavermectin $B_{1a}$ aglycone,
13-[5-(N-Ethoxycarbonyl)methylamino-2-indanyloxy]milbemycin $A_4$,
13-(5-Propoxycarbonylamino-2-indanyloxy)milbemycin $A_4$,
13-(5-Isopropoxycarbonylamino-2-indanyloxy)milbemycin $A_4$,
13-(5-Methanesulfonylamino-2-indanyloxy)milbemycin $A_4$,
13-(5-Methanesulfonylamino-2-indanyloxy)milbemycin $A_3$,
13-(5-Methanesulfonylamino-2-indanyloxy)milbemycin D,
13-Deoxy-13-(5-methanesulfonylamino-2-indanyloxy)-22,23-dihydroavermectin $B_{1a}$ aglycone,
13-[5-(N-Methanesulfonyl)methylamino-2-indanyloxy]milbemycin $A_3$,
13-(5-Ethanesulfonylamino-2-indanyloxy]milbemycin $A_4$,
13-[5-(3-Methylureido)-2-indanyloxy]milbemycin $A_4$,
13-[5-(3-Methylureido)-2-indanyloxy]milbemycin $A_3$,
13-[5-(3-Methylureido)-2-indanyloxy]milbemycin D,
13-Deoxy-13-[5-(3-methylureido)-2-indanyloxy]-22,23-dihydroavermectin $B_{1a}$ aglycone,
13-[(5-(1,3-Dimethylureido)-2-indanyloxy]milbemycin $A_4$,
13-[5-(3-Ethylureido)-2-indanyloxy]milbemycin $A_4$,
13-[5-(3-Ethylureido)-2-indanyloxy]milbemycin $A_3$,
13-[5-(3-Ethylureido)-2-indanyloxy]milbemycin D,
13-Deoxy-13-[5-(3-ethylureido)-2-indanyloxy]-22,23-dihydroavermectin $B_{1a}$ aglycone,
13-[5-(3-Ethyl-1-methylureido)-2-indanyloxy]milbemycin $A_4$,
13-[5-(3-Cyclopropylureido)-2-indanyloxy]milbemycin $A_4$,
13-[5-(3-Methylthioureido)-2-indanyloxy]milbemycin $A_4$,
13-[5-(3-Methylthioureido)-2-indanyloxy]milbemycin $A_3$,
13-[5-(3-Methylthioureido)-2-indanyloxy]milbemycin D,
13-Deoxy-13-[5-(3-methylthioureido)-2-indanyloxy]-22,23-dihydroavermectin $B_{1a}$ aglycone,
13-[5-(1,3-Dimethylthioureido)-2-indanyloxy]milbemycin $A_4$,
13-[5-(3-Phenylureido)-2-indanyloxy]milbemycin $A_4$,
13-[5-(3-Phenylureido)-2-indanyloxy]milbemycin $A_3$,
13-[5-(3-Phenylureido)-2-indanyloxy]milbemycin D,
13-Deoxy-13-[5-(3-phenylureido)-2-indanyloxy]-22,23-dihydroavermectin $B_{1a}$ aglycone,
13-[5-(1-Methyl-3-phenylureido)-2-indanyloxy]milbemycin $A_4$,
13-[5-(3,3-Dimethylcarbazoylamino)-2-indanyloxy]milbemycin $A_4$,
13-{2-[4-(1-Pyrrolidinylphenyl]ethoxy}milbemycin $A_4$,
13-[2-(4-Piperidinophenyl)ethoxy]milbemycin $A_4$,
13-{2-[4-(2-Oxoazetidin-1-yl)phenyl ]ethoxy}milbemycin $A_4$, 13-{2-[4-(2-Oxopyrrolidin-1-yl)phenyl]ethoxy}milbemycin A$_4$,
13-{2-[4-(2-Oxopiperid-1-yl)phenyl]ethoxy}milbemycin A$_4$,
13-{2-[4-(1,1-Dioxy-1,2-thiazolidin-2-yl)phenyl]ethoxy} milbemycin A$_4$,
13-{2-[4-(2-Oxo-1,3-oxazolidin-3-yl)phenyl]ethoxy} milbemycin A$_4$,
13-{2-[4-(2-Oxo-perhydro-1,3-oxazin-3-yl)phenyl]ethoxy}milbemycin A$_4$,
13-[2-(4-Succinimidophenyl)ethoxy]milbemycin A$_4$,
13-{2-[4-(2-Azaindan-2-yl)phenyl]ethoxy}milbemycin A$_4$,
13-{2-[4-(1,1-Dioxy-1-thia-2-azaindan-2-yl)phenyl]ethoxy}milbemycin A$_4$,
13-($\alpha$-Methylbenzyloxy)milbemycin A$_4$,
13-($\alpha$-Methylbenzyloxy)milbemycin A$_3$,
13-($\alpha$-Methylbenzyloxy)milbemycin D,
13-Deoxy-13-($\alpha$-methylbenzyloxy)-22,23-dihydroavermectin B$_{1a}$-aglycone,
13-($\alpha$-Ethylbenzyloxy)milbemycin A$_4$,
13-($\alpha,\alpha$-Dimethylbenzyloxy)milbemycin A$_4$,
13-(4-Fluoro-$\alpha$-methylbenzyloxy)milbemycin A$_4$,
13-($\alpha$-Methyl-4-methoxybenzyloxy)milbemycin A$_4$,
13-(4-Nitro-$\alpha$-methylbenzyloxy)milbemycin A$_4$,
13-(4-Amino-$\alpha$-methylbenzyloxy)milbemycin A$_4$,
13-(4-Cyanoacetamido-$\alpha$-methylbenzyloxy)milbemycin A$_4$,
13-(4-Methoxycarbonylamino-$\alpha$-methylbenzyloxy)-milbemycin A$_4$,
13-(4-Ethoxycarbonylamino-$\alpha$-methylbenzyloxy)milbemycin A$_4$,
13-(4-Methanesulfonylamino-$\alpha$-methylbenzyloxy)-milbemycin A$_4$,
13-(4-Ethanesulfonylamino-$\alpha$-methylbenzyloxy)milbemycin A$_4$,
13-[4-(3-Methylureido)-$\alpha$-methylbenzyloxy]milbemycin A$_4$,
13-[4-(3-Ethylureido)-$\alpha$-methylbenzyloxy]milbemycin A$_4$,
13-[4-(3-Cyclopropylureido)-$\alpha$-methylbenzyloxy]-milbemycin A$_4$,
13-[4-(3-Methylthioureido)-$\alpha$-methylbenzyloxy]milbemycin A$_4$, and
13-(1,2,3,4-Tetrahydronaphthalen-2-yloxy)milbemycin A$_4$.

Of the compounds listed above, the preferred compounds are:
13-t-Butoxymilbemycin A$_4$
13-Cyclopentyloxymilbemycin A$_4$
13-(4-Nitro-$\alpha$-methylbenzyloxy)milbemycin A$_4$
13-{2-[4-(2-Oxopyrrolidin-1-yl)phenyl]ethoxy}milbemycin A$_4$
13-{2-[4-(2-Oxopiperid-1-yl)phenyl]ethoxy}milbemycin A$_4$
13-{2-[4-(2-Oxo-1,3-oxazo lidin-3-yl)phenyl]ethoxy} milbemycin A$_4$
13-{2-[4-(1-Oxo-2-azaindan-2-yl)phenyl]ethoxy}milbemycin A$_4$
13-(5-Ethoxycarbonylamino-2-indanyloxy)milbemycin A$_4$
13-[5-(3-Methylureido)-2-indanyloxy]milbemycin A$_4$ and 13-[2-(4-Piperidinophenyl)ethoxy]milbemycin A$_4$ of which the most preferred compounds are:
13-t-Butoxymilbemycin A$_4$
13-{2-[4-(2-Oxo-1,3-oxazolidin-3-yl)phenyl]ethoxy} milbemycin A$_4$ and
13-[5-(3-Methylureido)-2-indanyloxy]milbemycin A$_4$.

Also preferred are salts, where available of the above compounds.

The compounds of the present invention may be prepared by a variety of processes known in the art for the preparation of compounds of this type. In general terms a suitable preparative procedure comprises subjecting a compound of formula (II) in either order to steps (a) and (b):

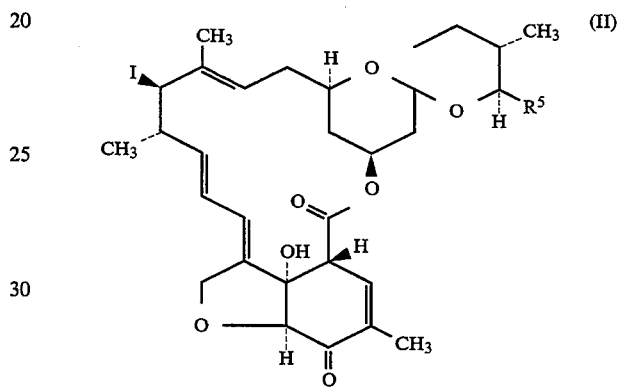

in which R$^5$ is as defined above, (a) reaction with an alcohol of formula (IIa):

R$^1$—OH         (IIa)

in which R$^1$ is as defined above; and (b) reaction either (b$^i$) with a reducing agent to reduce the oxygen atom at the 5-position to a hydroxy group, followed, if desired by reaction with an acylating agent, to give a compound of formula (I) in which X represents an alkanoyloxy group which has from 1 to 5 carbon atoms, and which is unsubstituted or has at least one substituent selected from the group consisting of substituents (d); or (b$^{ii}$) with hydroxylamine or with a salt thereof, to give a compound of formula (I) in which X represents a hydroxyimino group;

and then, if required, subjecting the product to one or both of steps (c) and (d):

(c) converting a group represented by R$^1$ to any other group so represented; and (d) salifying or esterifying the product.

In the above process, step (a) may be carried out before step (b), or step (b) may be carried out before step (a); we prefer that step (a) should be carried out before step (b).

In more detail, in this preferred embodiment, the compounds of formula (I) of the present invention can be prepared from a 13-iodo- milbemycin of formula (II) as shown in the following Reaction Scheme A:

Reaction Scheme A:

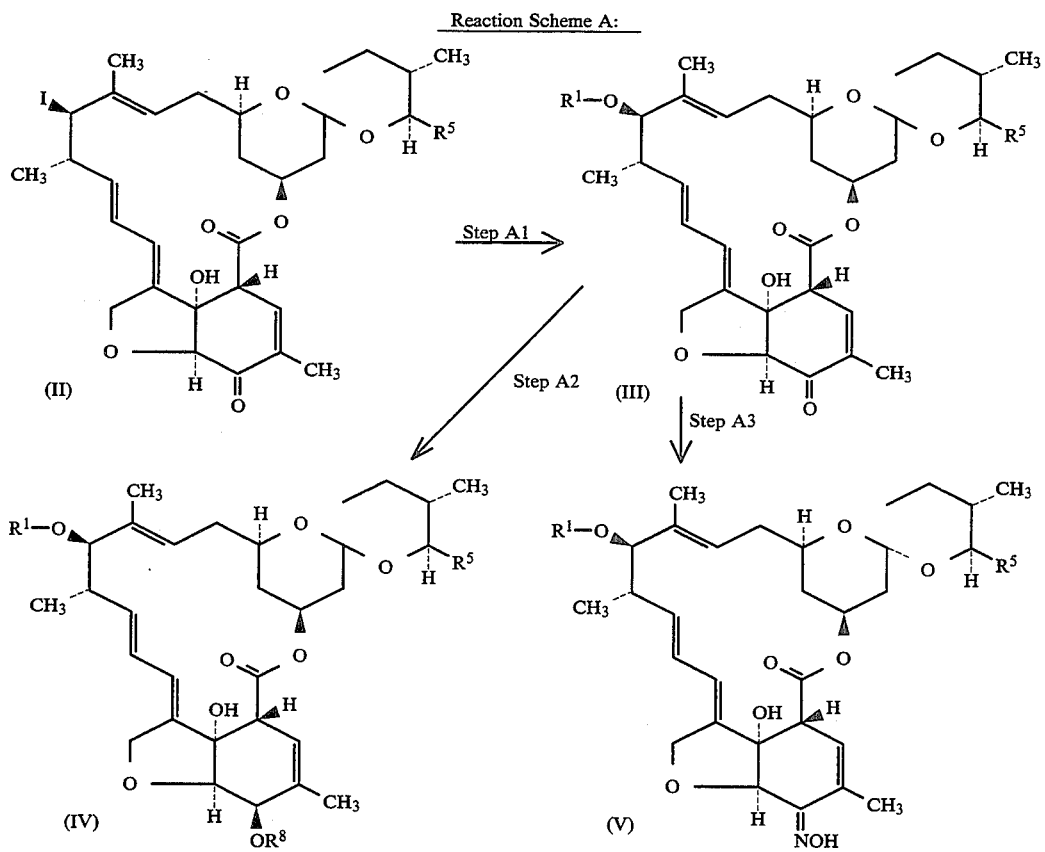

In the above formulae, $R^1$ and $R^5$ are as defined above and $R^8$ represents a hydrogen atom or a $C_1$–$C_5$ alkanoyl group or substituted $C_1$–$C_5$ alkanoyl group having at least one substituent selected from the group consisting of substituents (d), defined above (i.e. the alkanoyl groups defined above for the alkanoyloxy groups of X).

In Step A1, a compound of formula (III) is prepared by reacting a compound of formula (II) with an alcohol of formula (IIa) in the presence of a catalyst. Any catalyst capable of catalysing such etherification reactions, as are well known in the art, may equally be employed in this reaction, without any particular restriction. Examples of suitable catalysts include oxides and salts of mercury or silver, preferably a silver compound such as silver oxide, silver perchlorate or silver trifluoro- methanesulfonate, or a mercury compound such as mercury oxide, mercury iodide, mercury bromide or mercury trifluoromethanesulfonate.

In certain cases, the reaction may be accelerated by addition of an acid-binding agent. There is no particular limitation on the nature of such an acid-binding agent, provided that it has no adverse effect on the reaction, but 2,6-lutidine and calcium carbonate are preferred examples.

The reaction is normally and preferably effected in the presence of a solvent. There is no particular limitation on the nature of the solvent employed in the reaction, provided that it has no adverse effect on the reaction and that it is capable of solubilizing the starting compound, at least to some extent. Examples of suitable solvents include: aromatic hydrocarbons, such as benzene, toluene or xylene; halogenated hydrocarbons, especially halogenated aliphatic hydrocarbons, such as methylene chloride, 1,2-dichloroethane or chloroform; esters, such as ethyl acetate or propyl acetate; ethers, such as diethyl ether, tetrahydrofuran, dioxane or dimethoxyethane; amides, such as dimethylformamide, dimethylacetamide or hexamethylphosphoric triamide; and sulfoxides, such as dimethyl sulfoxide.

The reaction can take place over a wide range of temperatures, and the precise reaction temperature is not critical to the invention. In general, we find it convenient to carry out the reaction at a temperature from $-10°$ C. to $100°$ C., preferably from $0°$ C. to $50°$ C. The time required for the reaction may also vary widely, depending on many factors, notably the reaction temperature and the nature of the reagents and of the solvent. However, provided that the reaction is effected under the preferred conditions outlined above, a period of from 1 hour to 2 days will usually suffice.

After completion of the reaction, the reaction product may be recovered from the reaction mixture by conventional means. For example, the reaction mixture may be diluted with a water-immiscible organic solvent, after which, if necessary, the insoluble materials are removed by filtration. The filtrate may then be washed, for example successively with an aqueous solution of potassium iodide, an acid and water, and the solvent may be removed by distillation to afford the desired product. The product may, if required, be further purified by such conventional techniques as recrystallization or the various chromatography techniques, notably column chromatography.

In Step A2, a compound of formula (IV) is prepared by reducing the carbonyl group at the 5-position of the compound of formula (III) to a hydroxy group, which, if required, may then be subjected to acylation to give a compound of formula (IV) in which $R^8$ represents an alkanoyl group. There is no particular limitation on the nature of the reducing agent to be used in this reduction, provided that it can reduce the carbonyl group and has no adverse effect on the other functional groups in the compound of formula (III). Such reducing agents include, for example, hydride-producing agents, such as sodium borohydride or diborane, preferably sodium borohydride.

The reaction is normally and preferably effected in the presence of a solvent, and there is equally no particular limitation on the nature of the solvent, provided that it has no adverse effect on the reaction, but a lower alcohol (such as methanol, ethanol or propanol) is preferably used, especially when sodium borohydride is employed as the reducing agent.

The reaction can take place over a wide range of temperatures, and the precise reaction temperature is not critical to the invention. In general, we find it convenient to carry out the reaction at a temperature from 0° C. to 50° C. The time required for the reaction may also vary widely, depending on many factors, notably the reaction temperature and the nature of the reagents. However, provided that the reaction is effected under the preferred conditions outlined above, a period of from 5 minutes to 2 hours will usually suffice.

After completion of the reaction, the reaction product can be recovered easily from the reaction mixture by conventional means. For example, the reaction mixture may be diluted with a water-immiscible organic solvent and washed with water, after which the solvent may be removed by distillation to afford the desired product. The product may, if required, be further purified by such conventional techniques as recrystallization or the various chromatography techniques, notably column chromatography.

The reduction product thus prepared may, if required, be acylated to produce a compound in which $R^8$ is an alkanoyl group. This may take place in an inert solvent, using as the acylating agent an acid corresponding to the alkanoyl group which it is desired to introduce or using a reactive derivative of such an acid. The reaction can be carried out using conventional esterification techniques. Examples of suitable active derivatives of the acid include any of those commonly used for esterification such as acid halides (e.g. an acid chloride or acid bromide), acid anhydrides, mixed acid anhydrides, reactive esters (e.g. the N-hydroxybenztriazole ester) and reactive amides (e.g. the imidazolide).

Where the acid itself is employed, a dehydrating agent (such as dicyclohexylcarbodiimide, a-toluenesulfonic acid or sulfuric acid) is preferably also present. Where a reactive derivative of an acid is employed, an acid-binding agent is preferably also employed. There is no particular limitation on the nature of the acid-binding agent to be used, provided that it has the ability to eliminate an acid, for example, an organic amine such as triethylamine, N,N-diethylaniline, pyridine, 4-dimethylaminopyridine or 1,8-diazabicyclo[5.4.0]undecene-7, may be used.

There is no particular restriction on the nature of the solvent to be employed, provided that it has no adverse effect on the reaction or on the reagents involved and that it is capable of dissolving the reagents, at least to some extent. Examples of suitable solvents include: hydrocarbons, which may be aliphatic, aromatic or cycloaliphatic, such as hexane, benzene, toluene or xylene; halogenated hydrocarbons, especially halogenated aliphatic hydrocarbons, such as methylene chloride, 1,2-dichloroethane or chloroform; esters, such as ethyl acetate or propyl acetate; and ethers, such as diethyl ether, tetrahydrofuran, dioxane or dimethoxyethane.

After completion of the reaction, the reaction product can easily be recovered from the reaction mixture by conventional means. For example, the reaction mixture may be diluted with a water-immiscible organic solvent and washed successively with an acid, an alkali and water, after which the solvent may be removed by distillation to afford the desired product. The product may, if required, be further purified by such conventional techniques as recrystallization or the various chromatography techniques, notably column chromatography.

In Step A3 a compound of formula (V) is prepared by oximation at the 5-position of the compound of formula (III) with hydroxylamine or with a salt thereof (e.g. a salt with a mineral acid such as hydrochloric acid, nitric acid or sulfuric acid).

The reaction is usually carried out in an inert solvent, the nature of which is not critical, provided that it has no adverse effect on the reaction or on the reagents involved and that it is capable of dissolving the reagents, at least to some extent. Examples of suitable solvents include: alcohols, such as methanol or ethanol; ethers, such as tetrahydrofuran or dioxane; aliphatic acids, such as acetic acid; or a mixture of water with any one or more of these solvents.

The reaction can take place over a wide range of temperatures, and the precise reaction temperature is not critical to the invention. In general, we find it convenient to carry out the reaction at a temperature from 10° C. to 80° C. The time required for the reaction may also vary widely, depending on many factors, notably the reaction temperature and the nature of the reagents. However, provided that the reaction is effected under the preferred conditions outlined above, a period of from 1 to 24 hours will usually suffice.

After completion of the reaction, the reaction product can easily be recovered from the reaction mixture by conventional means. For example, the reaction mixture may be diluted with a water-immiscible organic solvent and washed with water, after which the solvent may be removed by distillation to afford the desired product. The product may, if required, be further purified by such conventional techniques as recrystallization or the various chromatography techniques, notably column chromatography.

As an alternative to the above, the reaction of step A2 or A3 may be carried out first, to prepare a compound in which X represents a hydroxy, alkanoyloxy or hydroxyimino group, after which the iodine atom at the 13 position is replaced by the appropriate ether group.

The compound of formula (IV) wherein $R^1$ is a group which includes an optionally substituted amino group can be prepared as illustrated in the following Reaction Scheme B:

Reaction Scheme B:

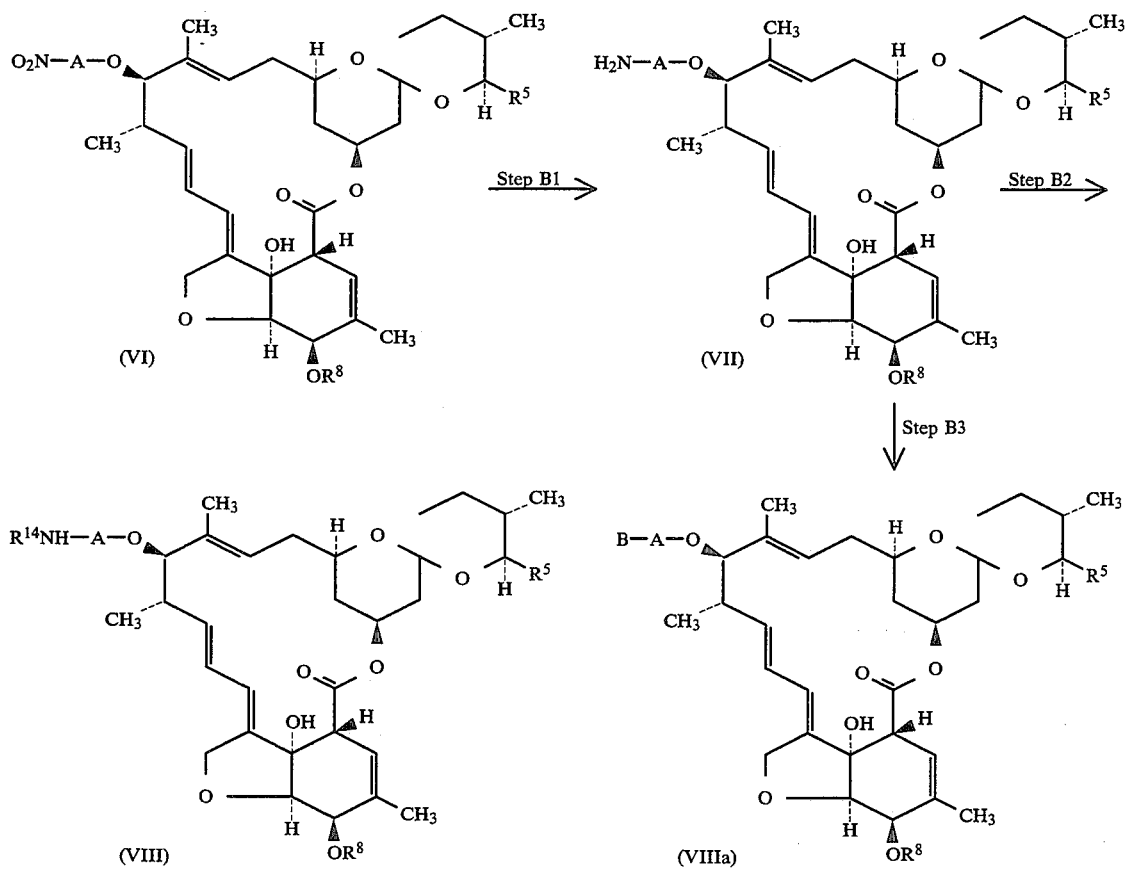

In the above formulae:
$R^5$ and $R^8$ are as defined above;
A represents a group of formula:

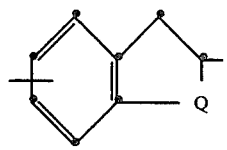

where Q is as defined above; or a group of formula:

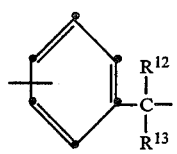

wherein $R^{12}$ and $R^{13}$ are as defined above;
$R^{14}$ represents a group of formula:

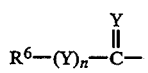

wherein $R^6$ is as defined above; Y represents an oxygen atom, a sulfur atom or an imino group; and n is 0 or 1, or a group of formula: $R^6S(O)_n-$, wherein $R^6$ is as defined above and n is 1 or 2;
and B represents a group of formula:

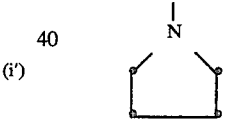

or a group of formula:

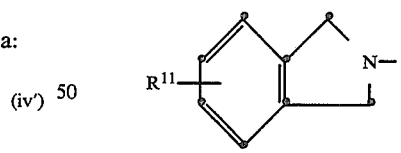

wherein $R^{11}$ is as defined above.

In Step B1 a compound of formula (VII) is prepared by reducing the nitro group of a compound of formula (VI) to give an amino group. This may by effected by a conventional reducing method for reducing a nitro group to an amino group. One such method is catalytic reduction using a precious metal catalyst. Examples of catalysts which are preferably employed include palladium-on-carbon, palladium-on-barium sulfate and platinum oxide.

The reaction is normally and preferably effected in the presence of a solvent, and there is no particular restriction on the nature of the solvent to be employed, provided that it has no adverse effect on the reaction or on the reagents involved. Examples of suitable solvents include: alcohols, such as methanol or ethanol; ethers, such as tetrahydrofuran or dioxane; and esters, such as ethyl acetate.

The reaction can take place over a wide range of temperatures, and the precise reaction temperature is not critical to the invention. In general, we find it convenient to carry out the reaction at a temperature from 10° C. to 80° C. The time required for the reaction may also vary widely, depending on many factors, notably the reaction temperature and the nature of the reagents. However, provided that the reaction is effected under the preferred conditions outlined above, a period of from 10 minutes to 5 hours will usually suffice.

An alternative preferred reducing method is reduction with zinc powder in acetic acid. This reaction is preferably carried out at a temperature ranging from 0° C. to room temperature, and the reaction time is usually in the range of from 10 minutes to 2 hours.

After completion of the reaction, the reaction product can easily be recovered from the reaction mixture by conventional means. For example, the reaction mixture may be diluted with a water-immiscible organic solvent, and the insoluble materials, if necessary, removed by filtration. The filtrate may then be washed with water, and the solvent may be removed by distillation to afford the desired product. The product may, if required, be further purified by such conventional techniques as recrystallization or the various chromatography techniques, notably column chromatography.

In Step B2 a compound of formula (VIII) is prepared by reacting the compound of formula (VII) with a reagent that is reactive with the amino group, to introduce the group represented by $R^{14}$.

The nature of the reagent to be employed will, of course, be dictated by the nature of the group $R^{14}$ which it is desired to introduce. However, in general, it may be a reactive derivative of a carboxylic acid of the type commonly used as an acylating agent such as an acid halide, an acid anhydride, a mixed acid anhydride, a reactive ester or a reactive amide. Alternatively, it may be: a chloroformate, such as methyl chloroformate or benzyl chloroformate; a thiochloroformate, such as ethyl chlorothioformate; a sulfonyl chloride, such as methanesulfonyl chloride or benzenesulfonyl chloride; an isocyanate; a thioisocyanate; or an imino ether. Alternatively, a carboxylic acid may be used as such, provided that it is activated, for example with dicyclohexylcarbodiimide.

When a halide, such as an acid halide, is employed as the reagent, it is usually preferred to carry out the reaction in the presence of an organic base, such as triethylamine, N,N-diethylaniline, pyridine, 4-dimethylaminopyridine or 1,8-diazabicyclo[5.4.0]undecene, as an acid-binding agent.

The reaction can take place over a wide range of temperatures, and the precise reaction temperature is not critical to the invention. In general, we find it convenient to carry out the reaction at a temperature from 0° C. to 80° C., preferably from 0° C. to room temperature. The time required for the reaction may also vary widely, depending on many factors, notably the reaction temperature and the nature of the reagents. However, provided that the reaction is effected under the preferred conditions outlined above, a period of from 10 minutes to 10 hours will usually suffice.

After completion of the reaction, the reaction product can easily be recovered from the reaction mixture by conventional means. For example, the reaction mixture may be diluted with a water-immiscible organic solvent, and the insoluble materials may then be removed, if required, by filtration and washed with water, after which the solvent may be removed by distillation to afford the desired product. The product may, if required, be further purified by such conventional techniques as recrystallization or the various chromatography techniques, notably column chromatography.

In Step B3, the compound of formula (VII) is reacted with a dialdehyde in the presence of a reducing agent to prepare a compound of formula (VIIIa).

The dialdehyde used will depend on the nature of the group B which it is desired to incorporate in the compound, however, examples include: aliphatic dialdehydes, such as succinic dialdehyde and glutaric dialdehyde; and aromatic dialdehydes, such as o-phthalic dicarboxaldehyde.

The reducing agent employed in this step is not particularly critical, provided that it can reduce the imide group and that it has no adverse effect on the other functional groups in the compound of formula (VII). Such reducing agents include hydride-type reducing agents such as sodium cyanoborohydride and diborane, preferably sodium cyanoborohydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; and ethers, such as tetrahydrofuran and dioxane.

The reaction can take place over a wide range of temperatures, and the precise reaction temperature is not critical to the invention. In general, we find it convenient to carry out the reaction at a temperature of from 0° to 80° C. The time required for the reaction may also vary widely, depending on many factors, notably the reaction temperature and the nature of the reagents. However, provided that the reaction is effected under the preferred conditions outlined above, a period of from 10 minutes to 5 hours will usually suffice.

After completion of the reaction, the reaction product can easily be collected from the reaction mixture by conventional means. For example, the reaction mixture may be diluted with a water-immiscible organic solvent, and, after the insolubles have been removed by filtration, if necessary, the filtrate is washed with water, followed by distillation of the solvent. The product may, if required, be further purified by conventional procedures, such as recrystallization and the various chromatography techniques, notably column chromatography.

The compound of formula (II), which is used as the starting material in the above sequences of reactions can advantageously be synthesized from 13-hydroxy-5-oxomilbemycin, which is represented by the general formula (IX), as illustrated in the following Reaction Scheme C:

Reaction Scheme C:

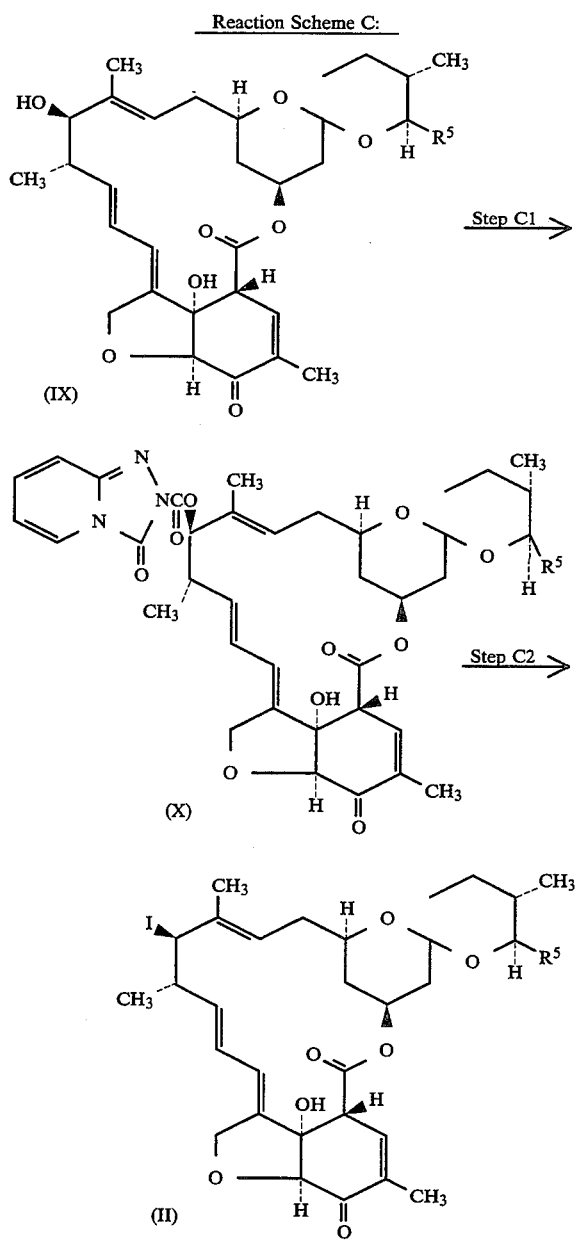

In the above formulae, $R^5$ is as defined above.

In Step C1 a compound of formula (X) is prepared by reacting the compound of formula (IX) with 2-chloroformyl-1,2,4-triazolo[4.3a]pyridin-3-one in the presence of an acid-binding agent.

There is no particular limitation on the nature of the acid-binding agent to be employed provided that it has the ability to eliminate any acid produced. For example, an organic amine, such as triethylamine, N,N-diethylaniline, pyridine, 4-dimethylaminopyridine or 1,8-diazabicyclo[5.4.0]undecene, may be used.

The reaction is also preferably effected in the presence of an inert solvent, the nature of which is not critical, provided that it has no adverse effect on the reaction or on the reagents involved. Examples of suitable solvents include: hydrocarbons, which may be aliphatic, aromatic or cycloaliphatic, such as hexane, benzene, toluene or xylene; halogenated hydrocarbons, especially halogenated aliphatic hydrocarbons, such as methylene chloride, 1,2-dichloroethane or chloroform; esters, such as ethyl acetate or propyl acetate; and ethers, such as diethyl ether, tetrahydrofuran, dioxane or dimethoxyethane.

The reaction can take place over a wide range of temperatures, and the precise reaction temperature is not critical to the invention. In general, we find it convenient to carry out the reaction at a temperature from 0° C. to 50° C. The time required for the reaction may also vary widely, depending on many factors, notably the reaction temperature and the nature of the reagents. However, provided that the reaction is effected under the preferred conditions outlined above, a period of from 5 minutes to 2 hours will usually suffice.

After completion of the reaction, the reaction product can easily be recovered from the reaction mixture by conventional means. For example, the reaction mixture may be diluted with a water-immiscible organic solvent, the insoluble materials may then be removed, if required, by filtration and washed, for example successively with an aqueous solution of potassium iodide, an acid and water, after which the solvent may be removed by distillation to afford the desired product.

In Step C2 13-iodomilbemycin, which is represented by formula (II), is prepared by reacting the compound of formula (X) with zinc iodide.

This reaction is usually carried out in a solvent. There is no particular restriction on the nature of the solvent to be employed, provided that it has no adverse effect on the reaction or on the reagents involved and that it is capable of dissolving the reagents, at least to some extent. Examples of suitable solvents include: hydrocarbons, which may be aliphatic, aromatic or cycloaliphatic, such as hexane, benzene, toluene or xylene; halogenated hydrocarbons, especially halogenated aliphatic hydrocarbons, such as methylene chloride, 1,2-dichloroethane or chloroform; esters, such as ethyl acetate or propyl acetate; and ethers, such as diethyl ether, tetrahydrofuran, dioxane or dimethoxyethane.

The reaction can take place over a wide range of temperatures, and the precise reaction temperature is not critical to the invention. In general, we find it convenient to carry out the reaction at a temperature from 0° C. to room temperature. The time required for the reaction may also vary widely, depending on many factors, notably the reaction temperature and the nature of the reagents. However, provided that the reaction is effected under the preferred conditions outlined above, a period of from 10 minutes to 2 hours will usually suffice.

After completion of the reaction, the reaction product can easily be recovered from the reaction mixture by conventional means. For example, the insoluble materials may be removed by filtration and the filtrate washed with water, after which the solvent may be removed by distillation to afford the desired product. The product may, if required, be further purified by such conventional techniques as recrystallization or the various chromatography techniques, notably column chromatography.

The compound of formula (IX), which is, therefore, the ultimate starting material for the above sequence of reactions, can be prepared from the natural or semisynthetic milbemycins or avermectins by the method disclosed in Japanese Patent Application Kokai No. Sho 61-103884.

The milbemycins and analogous natural products are generally obtained as mixtures at various ratios of related compounds, and they may be reacted after being separated into the various fractions or they may be used in the above reactions as mixtures, whether the natural mixture or an artificially produced mixture. Therefore, the compound used in each step of the above reactions may be either a single compound or a mixture of compounds. Accordingly, the compound of formula (I) may be prepared as a single compound or as a mixture of compounds, and, if prepared as a mixture of compounds, may be used as such or may be separated into the individual compounds prior to use.

The compounds of the invention have a strong acaricidal activity against, for example, adults, imagos and eggs of Tetranychus, Panonychus (e.g. *Panonychus ulmi* and *Panonychus citri*), *Aculopa pelekassi* and rust mites, which are parasitic to fruit trees, vegetables and flowers. They are also active against Ixodidae, Dermanyssidae and Sarcoptidae, which are parasitic to animals. Surprisingly, they have a strong activity even against acarids which are resistant to the known acaricides, which have recently started to become a great problem. Further, they are active against: ectoparasites, such as Oestrus, Lucilia, Hypoderma, Gautrophilus, lice and fleas, which are parasitic to animals and birds, particularly livestock and poultry; domestic insects, such as cockroaches and houseflies; and various harmful insects in agricultural and horticultural areas, such as aphids and larval Lepidoptera. They are also effective against Meloidogyne, Bursaphelenchus and Rhizoglyphus in the soil, and against insects of the orders Coleoptera, Homoptera, Heteroptera, Diptera, Thysanoptera, Orthoptera, Anoplura, Siphonaptera, Mallophage, Thysanura, Isoptera, Psocoptera, and Hvmenoptera.

The compounds of the invention equally can be used to control other plant-damaging insects, particularly insects that damage plants by eating them. The compounds can be used to protect both ornamental plants and productive plants, particularly cotton (e.g. against *Spodoptera littoralis* and *Heliothis virescens*), as well as vegetable crops (e.g. against *Leptinotarsa decemlineata* and *Myzus persicae*) and rice crops (e.g. against *Chilo suppressalis* and Laodelphax).

Accordingly, the compounds of the invention can be used to treat all manner of plants (as well as the seeds from which such plants are grown and the environment, whether for growth or storage, containing such plants) to protect them from insects such as those exemplified above. Such plants include cereals (e.g. maize or rice), vegetables (e.g. potatoes or soybeans), fruits and other plants (e.g. cotton).

The compounds of the invention can similarly be used to protect animals from a variety of ectoparasites, by applying the compounds to the animals or to the animals' environment, e.g. livestock housing, animal boxes, abattoirs, pasture land and other grasslands, as well as to any other places liable to be infested. The compounds may also be applied to external parts of the animals, preferably before they are infested.

Moreover, the compounds of the invention are effective against various parasitical helminths. These parasites can attack livestock, poultry and pet animals (such as pigs, sheep, goats, cows, horses, dogs, cats and fowl) and can cause grave economic damage. Among the helminths, the nematodes in particular often cause serious infection. Typical genera of nematodes which are parasitic on these animals and against which the compounds of the invention are effective include:

Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris.

Certain parasitical species of the genera Nematodirus, Cooperia and Oesophagostomum attack the intestines, while certain species of the genera Haemonchus and Ostertagia parasitize the stomach, and parasites belonging to the genus Dictyocaulus are found in the lungs. Parasites belonging to the families Filariidae and Setariidae are found in internal tissues and organs, for example, the heart, the blood vessels, the subcutaneous tissues and the lymphatic vessels. The compounds of the invention are active against all of these parasites.

The compounds of the invention are also effective against parasites which infect humans. Typical of the parasites which may most commonly be found in the digestive tracts of human beings are parasites of the genera:

Ancylostoma, Necator, Ascaris, Strongyloides, Trichinella, Capillaria, Trichuris and Enterobius.

The compounds are also active against parasites of the genera Wuchereria, Brugia, Onchocerca and Loa of the family Filariidae (which are found in blood, tissues and organs other than the digestive tract and are medically important), parasites of the genus Dracunculus of the family Dracunculidae and parasites of the genera Strongyloides and Trichinella, which in a particular state may parasitize outside the intestinal tract, although they are essentially intestinal parasites.

The form of the compositions of the invention and the nature of the carriers or diluents employed in them will vary depending upon the intended use of the composition. For example, where the compounds of the invention are to be employed as anthelmintics, they are preferably administered orally, parenterally or topically and the form of composition chosen will be appropriate to the intended route of administration.

For oral administration, the composition of the invention is preferably in the form of a liquid drink comprising a non-toxic solution, suspension or dispersion of the active compound in admixture with a suspending agent (such as bentonite), a wetting agent or other diluents, preferably in water or another non-toxic solvent. The drink, in general, also contains an anti-foaming agent. The active compound would normally be present in the drink in an amount of from 0.01 to 0.5% by weight, more preferably from 0.01 to 0.1% by weight.

Compositions for oral administration may also be in the form of dry solids, preferably in unit dosage form, such as capsules, pills or tablets containing the desired amount of the active compound. These compositions may be prepared by mixing the active compound uniformly with suitable diluents, fillers, disintegrators and/or binding agents, for example starch, lactose, talc, magnesium stearate and vegetable gum. The weight and contents of the preparation will vary widely, depending upon the nature of the animal to be treated, the degree of infection, the nature of the parasite and the body weight of the animal to be treated.

The compounds may also be administered as an additive to animal feedstuffs, in which case they may be dispersed uniformly in the feedstuffs, used as a top dressing or used in the form of pellets. The content of active compound in the feedstuff is preferably from 0.0001 to 0.02%, in order to achieve the desired anthelmintic activity.

For parenteral administration, the compound of the invention is preferably dissolved or suspended in a liquid vehicle, preferably a vegetable oil, such as peanut oil or cottonseed oil. Where the compound is a salt of a compound of formula (I), the liquid vehicle may be water or another aqueous medium. Depending upon the animal to be treated, the injection may be subcutaneous or into the proventriculus, a muscle or the trachea. Such preparations would normally contain the active compound at a concentration of from 0.05 to 50% by weight.

The compounds of the invention may also be administered topically in admixture with a suitable carrier, such as dimethyl sulfoxide or a hydrocarbon solvent. Such preparations would be applied directly to the outside of the animal by spraying (e.g. by a hand spray or in spray races), by dipping (e.g. in a plunge dip), by a pour-on solution or by manual methods (e.g. hand-dressing).

The dose of active compound may be varied, depending upon the nature of the animal to be treated, and the nature and degree of parasitic infection. However, best results for oral administration are achieved when the dose is from 0.01 to 100 mg, more preferably from 0.5 to 50 mg, per 1 kg body weight. The compound may be administered in a single dose or in divided doses for a relatively short period, such as from 1 to 5 days.

Where the composition of the invention is intended for agricultural or horticultural use, a variety of forms and formulations is possible. For example, the composition may be formulated as dusts, coarse dusts, soluble powders, microgranules, fine microgranules, wettable powders, dilute emulsions, emulsifiable concentrates, aqueous or oily suspensions, dispersions or solutions (which may be directly sprayable or for dilution), aerosols or capsules in, for example, polymeric substances. The carrier employed may be natural or synthetic and organic or inorganic; it is generally employed to assist the active compound to reach the substrate to be treated, and to make it easier to store, transport or handle the active compound. Solid, liquid and gaseous carriers may be employed, chosen from carriers well known in the art for use with compositions of this type.

Such formulations may be prepared by conventional means, e.g. by intimate mixing and/or grinding of the active ingredient(s) with the carrier or diluent, e.g. solvent, solid carrier or, optionally, surface-active agent.

Suitable solvents include: aromatic hydrocarbons, preferably the $C_8$ to $C_{12}$ fractions from petroleum distillation, such as xylene mixtures or substituted naphthalenes; esters of phthalic acid, such as dibutyl or dioctyl phthalate; aliphatic hydrocarbons, such as cyclohexane or the paraffins; alcohols and glycols or esters thereof, such as ethanol, ethylene glycol, ethylene glycol monomethyl ether or ethylene glycol monoethyl ether; ketones, such as cyclohexanone; strongly polar solvents, such as N-methyl-2-pyrrolidone, dimethyl sulfoxide or N,N-dimethylformamide; optionally epoxidized vegetable oils, such as epoxidized coconut oil or soybean oil; and water.

Solid carriers, which may be used, for example, in dusts and dispersible powders, include natural mineral fillers, such as calcite, talc, kaolin, montmorillonite or attapulgite. In order to improve the physical properties of the composition, it is also possible to add highly dispersed silicic acid or highly dispersed absorbent polymers. Suitable granulated adsorptive carriers may be porous (such as pumice, ground brick, sepiolite or bentonite) or non-porous (such as calcite or sand). A wide variety of pregranulated materials, organic or inorganic, may also be used; examples include dolomite and ground plant residues.

Surface-active agents which may be used are well known in the art and may be non-ionic, cationic or anionic agents having good emulsifying, dispersing and wetting properties. Mixtures of such agents may also be used.

Compositions may also contain stabilizers, anti-foaming agents, viscosity regulators, binders or adhesives or any combination thereof, as well as fertilizers or other active substances to achieve special effects.

Pesticidal compositions will generally contain: from 0.01 to 99%, more preferably from 0.1 to 95%, by weight of the active compound; from 1 to 99.99% of a solid or liquid additive; and from 0 to 25%, more preferably from 0.1 to 25%, of a surface-active agent. Whereas commercial products are generally sold as concentrated compositions, they are generally diluted by the end-user to a concentration of from 0.001 to 0.0001% by weight (from 10 to 1 ppm).

The invention is further illustrated by the following Examples, which illustrate the preparation of the compounds of the present invention, and the subsequent Test Examples, which illustrate the biological activity of the compounds of the invention. In the following Examples, all Nuclear Magnetic Resonance Spectra were measured at 270 MHz, unless otherwise stated.

EXAMPLE 1

13-(2-Cyclohexylethoxy)milbemycin $A_4$

1(a) 13-(2-Cyclohexylethoxy)-5-oxomilbemycin $A_4$ 0.333 g of 13-iodo-5-oxomilbemycin $A_4$ was dissolved in 2.50 ml of 1,2-dichloroethane, and 0.640 g of 2-cyclohexylethanol and 1.000 g of silver oxide were added to the resulting solution, after which the mixture was stirred at room temperature for 30 minutes. 30 ml of ethyl acetate were added to the reaction mixture, and the insoluble materials were removed by filtration using a Celite (trade mark) filter aid. The filtrate was then washed with a 10% w/v aqueous solution of sodium thiosulfate and with water, in that order, after which it was dried over anhydrous sodium sulfate. The solvent was then removed by distillation under reduced pressure. The resulting residue was purified by column chromatography through silica gel, eluted with a 1:4 by volume mixture of ethyl acetate and cyclohexane, to afford 0.242 g of the title compound.

1(b) 13-(2-Cyclohexylethoxy)milbemycin $A_4$ 0.121 g of 13-(2-cyclohexylethoxy)-5-oxomilbemycin $A_4$ [prepared as described in step (a) above] was dissolved in 5 ml of methanol, and 0.007 g of sodium borohydride was added to the resulting solution, whilst ice-cooling, after which the mixture was stirred for 30 minutes. 20 ml of ethyl acetate were then added to the reaction mixture, and the resulting mixture was washed twice with water and then dried over anhydrous sodium sulfate. The solvent was then removed by evaporation under reduced pressure. The resulting residue was purified by column chromatography through silica gel, eluted with a 3:7 by volume mixture of ethyl acetate and cyclohexane. The isomer substituted at the 15-position was then separated by reverse phase chromatography (through ODS; eluted with 85% v/v aqueous acetonitrile) to afford 0.075 g of the title compound. "ODS" is octadecylsilane.

Mass Spectrum m/z: 668 (M+, $C_{40}H_{60}O_8$).

Nuclear Magnetic Resonance Spectrum ($CDCl_3$), δ ppm:
1.88 (3H, singlet);
3.17 (1H, doublet, J=9.6 Hz);
3.96 (1H, doublet, J=6.2 Hz).

EXAMPLE 2

13-(2-Cyclohexylethoxy)milbemycin $A_4$ 5-oxime 0.121 g of 13-(2-cyclohexylethyloxy)-5-oxomilbemycin $A_4$ [prepared as described in Example 1(a)] was dissolved in 1.4 ml of methanol; and 0.70 ml of water, 1.4 ml of dioxan and 0.123 g of hydroxylamine hydrochloride were added to the resulting solution, after which the mixture was stirred at 35° C. for 3 hours. At the end of this time, 20 ml of ethyl acetate were added to the reaction mixture, and the resulting mixture was washed twice with water and then dried over anhydrous sodium sulfate. The solvent was then removed by evaporation under reduced pressure. The residue was purified by column chromatography through silica gel, eluted with a 1:3 by volume mixture of ethyl acetate and cyclohexane. The isomer substituted at the 15-position was then separated by reverse phase chromatography (through ODS; eluted with 85% v/v aqueous acetonitrile), to afford 0.075 g of the title compound.

Mass Spectrum m/z: 681 (M+, $C_{40}H_{59}NO_8$).

Nuclear Magnetic Resonance Spectrum ($CDCl_3$), δ ppm:
1.94 (3H, singlet);
3.18 (1H, doublet, J=9.9 Hz);
4.66 (1H, singlet).

EXAMPLE 3

13-Cyclohexyloxymilbemycin $A_4$

Following a procedure similar to that described in Example 1, but replacing the 2-cyclohexylethanol by cyclohexanol, the title compound was obtained.

Mass Spectrum m/z: 640 (M+, $C_{38}H_{56}O_8$).

Nuclear Magnetic Resonance Spectrum ($CDCl_3$), δ ppm:
1.87 (3H, singlet);
3.34 (1H, doublet, J=8.7 Hz);
3.96 (1H, doublet, J=6.2 Hz).

EXAMPLE 4

13-(5-Nitro-2-indanyloxy)milbemycin $A_4$

4(a) 5-Oxo-13-(5-nitro-2-indanyloxy)milbemycin $A_4$ 0.50 g of 13-iodo-5-oxomilbemycin $A_4$ was dissolved in 3.0 ml of 1,2-dichloroethane, and 1.00 g of 5-nitro-2-indanol and 0.52 g of mercuric iodide were added to the resulting solution, after which the mixture was stirred at room temperature for 2.5 hours. At the end of this time, 0.10 ml of 2,6-lutidine was added to the mixture and the mixture was stirred for a further 1 hour. 10 ml of ethyl acetate were then added to the reaction mixture, and insolubles were removed by filtration. The filtrate was then washed with a 10% w/v aqueous solution of potassium iodide (twice), with a 10% w/v aqueous solution of sodium thiosulfate and with water, in that order, after which it was dried over anhydrous sodium sulfate and the solvent was removed by evaporation under reduced pressure. The resulting residue was purified by column chromatography through silica gel, eluted with a 25:75 by volume mixture of ethyl acetate and hexane, to afford 0.39 g of the title compound.

4(b) 13-(5-Nitro-2-indanyloxy)milbemycin $A_4$ 0.39 g of 5-oxo-13-(5-nitro-2-indanyloxy)milbemycin $A_4$ [prepared as described in step (a) above] was dissolved in 7 ml of methanol, and 0.020 g of sodium borohydride was added to the resulting solution, whilst ice-cooling, after which the mixture was stirred for 20 minutes. 10 ml of ethyl acetate were then added to the reaction mixture, and the mixture was washed twice with water and then dried over anhydrous sodium sulfate. The solvent was then removed by evaporation under reduced pressure to afford 0.38 g of the title compound.

Mass Spectrum m/z: 719 (M+, $C_{41}H_{53}NO_{10}$).

Nuclear Magnetic Resonance Spectrum ($CDCl_3$), δ ppm:
1.88 (3H, singlet);
3.37 (1H, doublet, J=9.9 Hz);
3.96 (1H, doublet, J=6.2 Hz).

EXAMPLES 5 TO 27

The compounds of Examples 5 to 27 were prepared using the same procedures as described in Example 4.

EXAMPLE 5

13-Isobutoxymilbemycin $A_4$

Mass Spectrum m/z: 614 (M+, $C_{36}H_{54}O_8$).

Nuclear Magnetic Resonance Spectrum ($CDCl_3$) δ ppm: 1.87 (3H, Singlet);
3.18 (1H, doublet, J=9.8 Hz);
3.96 (1H, doublet, J=6.4 Hz).

EXAMPLE 6

13-t-Butoxymilbemycin $A_4$

Mass Spectrum m/z: 614 (M+, $C_{36}H_{54}O_8$).

Nuclear Magnetic Resonance Spectrum ($CDCl_3$), δ ppm:
1.16 (9H, singlet);
1.87 (3H, singlet);
3.57 (1H, doublet, J=9.8 Hz);
3.95 (1H, doublet, J=5.9 Hz).

EXAMPLE 7

13-sec-Butoxymilbemycin $A_4$

Mass Spectrum m/z: 614 (M+, $C_{36}H_{54}O_8$).

Nuclear Magnetic Resonance Spectrum ($CDCl_3$), δ ppm:
1.87 (3H, singlet);
3.32 (1H, doublet, J=9.8 Hz);
3.96 (1H, doublet, J=6.2 Hz).

EXAMPLE 8

13-1,1-Dimethylpropoxy)milbemycin $A_4$

Mass Spectrum m/z: 628 (M+, $C_{37}H_{56}O_8$).

Nuclear Magnetic Resonance Spectrum ($CDCl_3$), δ ppm:
1.87 (3H, singlet);
3.57 (1H, doublet, J=9.8 Hz);
3.96 (1H, doublet, J=6.4 Hz).

EXAMPLE 9

13-(1,2-Dimethylpropoxy)milbemycin $A_4$

Mass Spectrum m/z: 628 (M+, $C_{37}H_{56}O_8$).

Nuclear Magnetic Resonance Spectrum (CDCl$_3$), δ ppm:
1.87 (3H, singlet);
3.33 (1H, doublet, J=9.8 Hz);
3.96 (1H, doublet, J=6.3 Hz).

EXAMPLE 10

13-(1,2,2-Trimethylpropoxy)milbemycin A$_4$

Mass Spectrum m/z: 642 (M+, C$_{38}$H$_{58}$O$_8$).
Nuclear Magnetic Resonance Spectrum (CDCl$_3$), δ ppm:
1.87 (3H, singlet);
3.32 (1H, doublet, J=9.9 Hz);
3.96 (0.5H, doublet, J=6.4 Hz);
3.96 (0.5H, doublet, J=5.9 Hz).

EXAMPLE 11

13-(3,3-Dimethylbutoxy)milbemycin A$_4$

Mass Spectrum m/z: 642 (M+, C$_{38}$H$_{58}$O$_8$).
Nuclear Magnetic Resonance Spectrum (CDCl$_3$), δ ppm:
1.87 (3H, singlet);
3.19 (1H, doublet, J=9.5 Hz);
3.96 (1H, doublet, J=6.6 Hz).

EXAMPLE 12

13-Neopentyloxymilbemycin A$_4$

Mass Spectrum m/z: 628 (M+, C$_{37}$H$_{56}$O$_8$).
Nuclear Magnetic Resonance Spectrum (CDCl$_3$), δ ppm:
1.87 (3H, singlet);
3.14 (1H, doublet, J=9.5 Hz);
3.96 (1H, doublet, J=6.2 Hz).

EXAMPLE 13

13-Cyclobutyloxymilbemycin A$_4$
Mass Spectrum m/z: 612 (M+, C$_{36}$H$_{52}$O$_8$).
Nuclear Magnetic Resonance Spectrum (CDCl$_3$), δ ppm:
1.88 (3H, singlet);
3.20 (1H, doublet, J=9.9 Hz);
3.96 (1H, doublet, J=6.2 Hz).

EXAMPLE 14

13-Cyclopentyloxymilbemycin A$_4$

Mass Spectrum m/z: 626 (M+, C$_{37}$H$_{54}$O$_8$).
Nuclear Magnetic Resonance Spectrum (CDCl$_3$), δ ppm:
1.88 (3H, singlet);
3.26 (1H, doublet, J=9.9 Hz);
3.96 (1H, doublet, J=6.2 Hz).

EXAMPLE 15

13-Cyclopentylmethoxymilbemycin A$_4$

Mass Spectrum m/z: 640 (M+, C$_{38}$H$_{56}$O$_8$).
Nuclear Magnetic Resonance Spectrum (CDCl$_3$), δ ppm:
1.88 (3H, singlet);
3.18 (1H, doublet, J=9.9 Hz);
3.96 (1H, doublet, J=6.2 Hz).

EXAMPLE 16

13-(2-Indanyloxy)milbemycin A$_4$

Mass Spectrum m/z: 674 (M+, C$_{41}$H$_{54}$O$_8$).
Nuclear Magnetic Resonance Spectrum (CDCl$_3$), δ ppm:
1.88 (3H, singlet);
3.38 (1H, doublet, J=9.9 Hz);
3.96 (1H, doublet, J=6.2 Hz).

EXAMPLE 17

13-(1,2,3,4-Tetrahydronaphthalen-2-yloxy)milbemycin A$_4$

Mass Spectrum m/z: 688 (M+, C$_{42}$H$_{56}$O$_8$).
Nuclear Magnetic Resonance Spectrum (CDCl$_3$), δ ppm:
1.88 (3H, singlet);
3.47 (1H, doublet, J=9.8 Hz);
3.96 (1H, doublet, J=6.4 Hz).

EXAMPLE 18

13-[(R)]-α-Methylbenzyloxy]milbemycin A$_4$

Mass Spectrum m/z: 662 (M+, C$_{40}$H$_{54}$O$_8$).
Nuclear Magnetic Resonance Spectrum (CDCl$_3$) δ ppm:
1.86 (3H, singlet);
3.12 (1H, doublet, J=9.9 Hz);
3.94 (1H, doublet, J=6.2 Hz);
4.32 (1H, quartet, J=6.2 Hz).

EXAMPLE 19

13-[(S)-α-Methylbenzyloxy]milbemycin A$_4$

Mass Spectrum m/z: 662 (M+, C$_{40}$H$_{54}$O$_8$).
Nuclear Magnetic Resonance Spectrum (CDCl$_3$), δ ppm:
1.87 (3H, singlet);
3.47 (1H, doublet, J=9.9 Hz);
3.95 (1H, doublet, J=6.2 Hz);
4.33 (1H, quartet, J=6.3 Hz).

EXAMPLE 20

13- (α-Ethylbenzyloxy)milbemycin A$_4$

Mass Spectrum m/z: 676 (M+, C$_{41}$H$_{56}$O$_8$).
Nuclear Magnetic Resonance Spectrum (CDCl$_3$), δ ppm:
1.87 (3H, singlet);
3.11 (1H, doublet, J=9.8 Hz);
3.95 (1H, doublet, J=6.2 Hz).

EXAMPLE 21

13-(4-Nitro-α-methylbenzyloxy)milbemycin A$_4$

Mass Spectrum m/z: 707 (M+, C$_{40}$H$_{52}$NO$_{10}$).
Nuclear Magnetic Resonance Spectrum (CDCl$_3$), δ ppm:
1.87 (3H, singlet);
3.07 (0.5H, doublet, J=9.5 Hz);
3.49 (0.5H, doublet, J=9.5 Hz);
3.95 (0.5H, doublet, J=5.9 Hz);
3.96 (0.5H, doublet, J=6.6 Hz).

EXAMPLE 22

13-{2-[4-(2-Oxoazetidin-1-yl}phenyl]ethoxy}milbemycin A$_4$

Mass Spectrum m/z: 695 (M+ −32). Nuclear Magnetic Resonance Spectrum (CDCl$_3$), δ ppm:
1.87 (3H, singlet);
3.10 (2H, doublet, J=4.4 Hz);
3.20 (1H, doublet, J=9.8 Hz);

3.61 (2H, doublet, J=4.4 Hz);
3.96 (1H, doublet, J=6.4 Hz).

EXAMPLE 23

13-{2-[4-(2-Oxopyrrolidin-1-yl)phenyl]ethoxy}milbemycin $A_4$

Mass Spectrum m/z: 745 (M+, $C_{44}H_{59}NO_9$).
Nuclear Magnetic Resonance Spectrum ($CDCl_3$), δ ppm:
1.87 (3H, singlet);
2.60 (2H, multiplet);
3.21 (1H, doublet, J=9.8 Hz);
3.84 (2H, multiplet);
3.98 (1H, doublet, J=6.4 Hz).

EXAMPLE 24

13-{2-[4-(2-Oxopiperid-1-yl)phenyl]ethoxy}milbemycin $A_4$

Mass Spectrum m/z: 741 (M+ −18).
Nuclear Magnetic Resonance Spectrum ($CDCl_3$), δ ppm:
1.87 (3H, singlet);
2.55 (2H, multiplet);
3.22 (1H, doublet, J=9.8 Hz);
3.60 (2H, multiplet);
3.96 (1H, doublet, J=6.4 Hz).

EXAMPLE 25

13-{2-[4-(2-Oxo-1,3-oxazolidin-3-yl)phenyl]ethoxy} milbemycin $A_4$

Nuclear Magnetic Resonance Spectrum ($CDCl_3$), δ ppm:
1.87 (3H, singlet);
3.21 (1H, doublet, J=9.8 Hz);
3.95 (1H, doublet, J=6.3 Hz);
4.04 (2H, multiplet);
4.47 (2H, multiplet).

EXAMPLE 26

13-{2-[4-(1-Oxo-2-azaindan-2-yl)phenyl]ethoxy}milbemycin A4

Mass Spectrum m/z: 757 (M+ −18).
Nuclear Magnetic Resonance Spectrum ($CDCl_3$), δ ppm:
1.87 (3H, singlet);
3.23 (1H, doublet, J=9.8 Hz);
3.96 (1H, doublet, J=6.4 Hz);
4.85 (2H, multiplet).

EXAMPLE 27

13-{2-[4-(1,1-Dioxy-1-thia-2-azaindan-2-yl)phenyl]ethoxy}milbemycin $A_4$

Nuclear Magnetic Resonance Spectrum ($CDCl_3$), δ ppm:
1.87 (3H, singlet);
3.14 (1H, doublet, J=9.8 Hz);
3.96 (1H, doublet, J=6.4 Hz);
5.06 (2H, singlet).

EXAMPLE 28

13-(5-Amino-2-indanyloxy)milbemycin $A_4$ 0.38 g of 13-(5-nitro-2-indanyloxy)milbemycin $A_4$ (prepared as described in Example 4) was dissolved in 4 ml of 90% v/v aqueous acetic acid, and 0.40 g of zinc powder was added to the resulting solution, whilst ice-cooling. The resulting mixture was then stirred for 20 minutes. At the end of this time, 20 ml of ethyl acetate were added to the reaction mixture, and insolubles were removed by filtration. The filtrate was then washed with water three times, and dried over anhydrous sodium sulfate. The solvent was then removed by evaporation under reduced pressure. The residue was purified by column chromatography (through ODS; eluted with 75% v/v aqueous acetonitrile), to afford 0.34 g of the title compound.

Nuclear Magnetic Resonance Spectrum ($CDCl_3$), δ ppm:
1.88 (3H, singlet);
3.36 (1H, doublet, J=9.9 Hz);
3.96 (1H, doublet, J=6.2 Hz).

EXAMPLE 29

13 -(4 -Amino-α-methylbenzyloxy)milbemycin $A_4$ 13-(4-Nitro-α-methylbenzyloxy)milbemycin $A_4$ obtained as described in Example 21 was treated in the same manner as described in Example 28 to afford the title compound.

EXAMPLE 30

13-(5-Ethoxycarbonylamino-2-indanyloxy)milbemycin $A_4$ 0.130 g of 13-(5-amino-2-indanyloxy)milbemycin $A_4$ (prepared as described in Example 28) was dissolved in 1.5 ml of 1,2-dichloroethane, and 0.016 ml of pyridine and 0.022 g of ethyl chloroformate were added to the resulting solution, after which the mixture was stirred at room temperature for 1 hour. At the end of this time, the reaction mixture was diluted with ethyl acetate, washed with 0.1N aqueous hydrochloric acid, with water, with a 4% w/v aqueous solution of sodium hydrogencarbonate and with water, in that order, after which it was dried over anhydrous sodium sulfate. The solvent was then removed by evaporation under reduced pressure. The residue was purified by column chromatography (through ODS; eluted with 80% v/v aqueous acetonitrile), to afford 0.118 g of the title compound.

Mass Spectrum m/z: 761 (M+, $C_{44}H_{59}NO_{10}$).
Nuclear Magnetic Resonance Spectrum ($CDCl_3$), δ ppm:
1.88 (3H, singlet);
3.35 (0.5H, doublet, J=9.5 Hz);
3.36 (0.5H, doublet, J=9.9 Hz);
3.96 (1H, doublet, J=6.2 Hz);
4.21 (2H, quartet, J=7.2 Hz).

EXAMPLES 31 AND 32

The compounds of Examples 31 to 32 were prepared by the same procedures as described in Example 30 above.

EXAMPLE 31

13-(4-Methanesulfonylamino-α-methylbenzyloxy)-milbemycin $A_4$

Nuclear Magnetic Resonance Spectrum ($CDCl_3$), δ ppm:
1.87 (3H, singlet);
2.99 (1.5H, singlet);
3.03 (1.5H, singlet);
3.09 (0.5H, doublet, J=9.8 Hz);
3.47 (0.5H, doublet, J=9.9 Hz);

3.94 (0.5H, doublet, J=6.4 Hz);
3.96 (0.5H, doublet, J=6.4 Hz);
4.3–4.4 (1H, multiplet).

EXAMPLE 32

13-(4-Cyanoacetylamino-α-methylbenzyloxy)milbemycin A$_4$

Mass Spectrum m/z: 744 (M+, C$_{43}$H$_{56}$N$_2$O$_9$).
Nuclear Magnetic Resonance Spectrum (CDCl$_3$), δ ppm:
1.87 (3H, singlet);
3.08 (1H, doublet, J=9.8 Hz);
3.55 (1H, singlet);
3.56 (1H, singlet);
3.94 (1H, doublet, J=6.3 Hz);
4.2–4.4 (1H, multiplet).

EXAMPLE 33

13-[5-(3-Methylureido)-2-indanyloxy]milbemycin A$_4$ 0.130 g of 13-(5-amino-2-indanyloxy)milbemycin A$_4$ (prepared as described in Example 28) was dissolved in 1.5 ml of tetrahydrofuran, and 2 droplets of methyl isocyanate were added to the resulting solution, after which the mixture was stirred for 1.5 hours. At the end of this time, the solvent and the excess of methyl isocyanate were removed from the reaction mixture by evaporation under reduced pressure, and the residue was dissolved in 20 ml of ethyl acetate. The resulting solution was then washed with water and dried over anhydrous sodium sulfate, after which the solvent was removed by evaporation under reduced pressure. The residue was purified by column chromatography (through ODS; eluted with 80% v/v aqueous acetonitrile), to afford 0.136 g of the title compound.

Nuclear Magnetic Resonance Spectrum (CDCl$_3$), δ ppm:
1.87 (3H, singlet);
3.21 (1H, doublet, J=9.9 Hz);
3.95 (1H, doublet, J=6.2 Hz);
6.56 (1H, singlet);
6.61 (1H, singlet).

EXAMPLES 34 AND 35

The compounds of Examples 34 and 35 were prepared by the same procedures as described in Example 33 above.

EXAMPLE 34

13-[4-(3-Methylureido)-α-methylbenzyloxy]milbemycin A$_4$

Mass Spectrum m/z: 703 (M+ −31).
Nuclear Magnetic Resonance Spectrum (CDCl$_3$), δ ppm:
1.87 (3H, singlet);
2.83 (1.5H, doublet, J=5.4 Hz);
2.85 (1.5H, doublet, J=5.4 Hz);
3.11 (0.5H, doublet, J=9.8 Hz);
3.47 (0.5H, doublet, J=9.8 Hz);
3.93 (0.5H, doublet, J=5.9 Hz);
3.96 (0.5H, doublet, J=6.4 Hz);
4.01–4.34 (1H, multiplet).

EXAMPLE 35

13-[4-(3-Methylthioureido)-α-methylbenzyloxy]milbemycin A$_4$

Mass Spectrum m/z: 761 (M+, C$_{44}$H$_{59}$NO$_{10}$).
Nuclear Magnetic Resonance Spectrum (CDCl$_3$), δ ppm:
1.87 (3H, singlet);
3.13–3.17 (3H, multiplet);
3.10 (0.5H, doublet, J=10.25 Hz);
3.49 (0.5H, doublet, J=9.8 Hz);
3.94 (0.5H, doublet, J=6.4 Hz);
3.96 (0.5H, doublet, J=5.9 Hz);
4.29–4.39 (1H, multiplet).

EXAMPLE 36

13-[2-(4-Piperidinophenyl)ethoxy]milbemycin A$_4$ 0.130 g of 13-(4-amino-phenethyloxy)- milbemycin A$_4$ (prepared as described in Example 29) was dissolved in 1.5 ml of methanol, and 0.040 ml of glutaric dialdehyde was added to the resulting solution, after which the mixture was stirred at room temperature overnight. The reaction mixture was then diluted with 20 ml of ethyl acetate, and washed with water, with a 4% w/v aqueous solution of sodium hydrogencarbonate and with water, in that order, after which it was dried over anhydrous sodium sulfate. The solvent was then removed by evaporation under reduced pressure. The residue was purified by column chromatography (through ODS; eluted with 80% v/v aqueous acetonitrile), to afford 0.090 g of the title compound.

Mass Spectrum m/z: 745 (M+, C$_{45}$H$_{63}$NO$_8$).
Nuclear Magnetic Resonance Spectrum (CDCl$_3$), δ ppm:
1.87 (3H, singlet);
3.08–3.12 (4H, multipier);
3.22 (1H, doublet, J=9.8 Hz);
3.96 (1H, doublet, J=6.4 Hz).

EXAMPLES 37 AND 38

The compounds of Examples 37 and 38 were prepared by the same procedures as described in Example 36 above.

EXAMPLE 37

13-{2-[4-(1-Pyrrolidinyl)phenyl]ethoxy}milbemycin A$_4$

Mass Spectrum m/z: 731 (M+C$^{44}$H$^{61}$NO$_8$).
Nuclear Magnetic Resonance Spectrum (CDCl$_3$), δ ppm:
1.87 (3H, singlet);
3.21–3.26 (4H, multiplet);
3.96 (1H, doublet, J=6.4 Hz).

EXAMPLE 38

13-{2-[4-(2-Azaindan-2-yl)phenyl]ethoxy}milbemycin A$_4$

Mass Spectrum m/z: 745 (M+, C$_{45}$H$_{63}$NO$_8$).
Nuclear Magnetic Resonance Spectrum (CDCl$_3$), δ ppm:
1.87 (3H, singlet);
3.24 (1H, doublet, J=10.3 Hz);
3.96 (1H, doublet, J=6.4 Hz);
4.64 (4H, singlet).

EXAMPLE 39

13-(4-Methyl-α-methylbenzyloxy)milbemycin A₄

The procedure described in Example 4 was repeated, except that 4-methyl-α-methylbenzyl alcohol was used in place of 5-nitro-2-indanol to give the title compound.

Mass Spectrum m/z: 676 (M+, $C^{41}H^{56}NO^8$).

Nuclear Magnetic Resonance Spectrum (CDCl₃), δ ppm:
1.87 (3H, singlet);
2.36 (3H, singlet);
3.11 (0.5H, doublet, J=9.8 Hz);
3.46 (0.5H, doublet, J=10.3 Hz);
3.94 (0.5H, doublet, J=6.3 Hz);
3.96 (0.5H, doublet, J=5.9 Hz)
4.2–4.0 (1H, multiplet).

EXAMPLE 40

13-(6-Nitro-1,2,3,4-tetrahydronaphthalen-2-yloxy)-milbemycin A₄

The procedure described in Example 4 was repeated, except that 2-hydroxy-6-nitro-1,2,3,4-tetrahydronaphthalene was used in place of 5-nitro-2-indanol to give the title compound.

Mass Spectrum m/z: 733 (M+, $C_{42}H_{55}NO_{10}$).

Nuclear Magnetic Resonance Spectrum (CDCl₃), δ ppm:
1.87 (3H, singlet);
2.70–3.20 (2H, multiplet)
3.43 (1H, doublet, J=9.8 Hz);
3.95 (1H, doublet, J=6.3 Hz);
7.20 (1H, doublet, J=8.8 Hz);
7.93 (1H, doublet of doublets, J=2.4 & 8.8 Hz);
7.96 (1H, doublet, J=2.4 Hz).

TEST EXAMPLES

The anthelmintic activity against *Nippostongylus brasiliensis*, a nematode parasitic to rats, was examined with groups each containing 3 Wistar strain rats of body weight in the range from 40 to 60 g.

The rats were infested percutaneously with about 100 larvae of the nematode for each rat. Solutions containing the test compound at various concentrations were administered orally 3 days after infection. Each solution was prepared by dissolving 1.0 mg of the test compound in 0.1 ml of dimethylformamide, and then adding 10 ml of polyethylene glycol (PEG 400) to the solution. The solution was then adjusted by the addition of PEG 400 to achieve a concentration of 0.250 or 0.125 mg/kg.

The rats were killed 4 days after infection, and the number of parasites in the small intestine was counted. The results obtained are summarized in Table 1.

In the Table, the anthelmintic activity was calculated by the following formula:

Anthelmintic activity (%) =

$$100 \times \frac{\text{Number of parasites} - \text{Number of parasites}}{\text{Number of parasites in untreated infected group}}$$

TABLE 1

| | Effects of the compounds administered orally | |
|---|---|---|
| | Anthelmintic activity (%)* | |
| | 0.250** | 0.125** |
| 1) Compound of Example 6 | 84.8 | 62.8 |
| 2) Compound of Example 16 | 99.2 | 73.3 |
| 3) Compound of Example 17 | — | 89.8 |
| 4) Compound of Example 18 | 93.3 | 57.1 |
| 5) Compound of Example 19 | 96.2 | — |
| 6) Compound of Example 21 | — | 93.5 |
| 7) Compound of Example 23 | — | 91.2 |
| 8) Compound of Example 24 | — | 97.3 |
| 9) Compound of Example 25 | — | 96.9 |
| 10) Compound of Example 30 | — | 97.6 |
| 11) Compound of Example 33 | — | 98.0 |
| 12) Compound of Example 36 | — | 87.6 |
| 13) 13-Methoxymilbemycin A₄*** | 44.0 | 49.5 |
| 14) Milbemycin A₄ | 24.8 | — |

**Dose: mg/kg
***Compound disclosed in U.S. Pat. No. 4 696 945.

In the above Table, a dash means that the compound was not tested at the particular concentration.

We claim:

1. A compound of the formula (I):

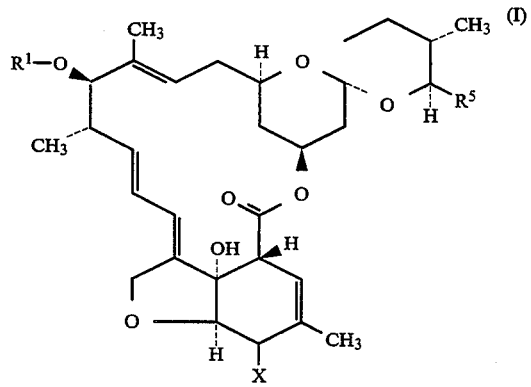

in which:

R¹ represents: a cycloalkyl group having from 4 to 8 carbon atoms; an alkyl group having from 1 to 4 carbon atoms and substituted by a cycloalkyl group having from 3 to 8 carbon atoms, said cycloalkyl group being unsubtituted or having at least one substituent selected from the group consisting of substituents (c); or a group having the following formula:

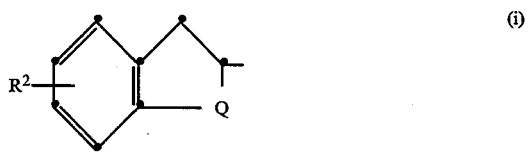

wherein:

R² represents: a hydrogen atom; a halogen atom; a cyano group; a nitro group; an alkyl group having from 1 to 4 carbon atoms; a substituted alkyl group which has from 1 to 4 carbon atoms and which has at least one substituent selected from the group consisting of substituents (a); an alkoxy group having from 1 to 4 carbon atoms; an alkoxyalkoxy group having a total of from 2 to 6 carbon atoms; or a group having one of the following formulae:
—$(CH_2)_n NHR^9$
—$(CH_2)_n NR^9 COR^6$ —$(CH_2)_nNR^9COCOR^6$
—$(CH_2)_nNR^9COCOOR^7$
—$(CH_2)_nNR^9CHR^6NHCOR^6$
—$(CH_2)_nNR^9CHR^6NHCONHR^6$
—$(CH_2)_nNR^9CHR^6NHCOOR^7$
—$(CH_2)_nNR^9C(=Y)YR^6$
—$(Ch_2)_nNR^9C(=Y)NR^6R^6$
—$(CH_2)_nNR^9C(=Y)NR^6NR^6R^6$
—$(CH_2)_nNR^9C(=Y)NR^6NHZ$
—$(CH_2)_nNR^9C(=NR^{10})NHR^{10}$
—$(CH_2)_nNR^9C(=NR^{10})R^6$ or
—$(CH_2)_nNR^9SO_mR^6$
wherein:
m is 1 or 2;
n is 0, 1 or 2;
$R^6$ represents a hydrogen atom; an alkyl group having from 1 to 8 carbon atoms; a substituted alkyl group having from 1 to 8 carbon atoms and having at least one substituent selected from the group consisting of substituents (b); an aliphatic hydrocarbon group having from 2 to 8 carbon atoms and having one or two carbon-carbon double or triple bonds; a cycloalkyl group having from 3 to 8 carbon atoms; a substituted cycloalkyl group having from 3 to 8 carbon atoms and having at least one substituent selected from the group consisting of substituents (c); an aryl group which has from 6 to 14 ring carbon atoms and which is unsubstituted or which has at least one substituent selected from the group consisting of substituents (c); an aryloxy group which has from 6 to 14 ring carbon atoms and which is unsubstituted or which has at least one substituent selected from the group consisting of substituents (c); an arylthio group which has from 6 to 14 ring carbon atoms and which is unsubstituted or which has at least one substituent selected from the group consisting of substituents (c); and, where there are two or more groups or atoms represented by $R^6$, these are the same or different from each other;
$R^7$ represents an alkyl group having from 1 to 4 carbon atoms, a cycloalkyl group having from 3 to 7 carbon atoms, or an aralkyl group in which an alkyl group having from 1 to 4 carbon atoms is substituted by from 1 to 3 aryl groups which have from 6 to 10 ring carbon atoms and which have at least one substituent selected from the group consisting of substituents (c);
$R^9$ represents a hydrogen atom or an alkyl group having from 1 to 4 carbon atoms;
$R^{10}$ represents any of the groups or atoms defined above for $R^6$, or it represents a cyano group, a nitro group, a group of formula —$COOR^7$, wherein $R^7$ is as defined above, or a group of formula —$COR^6$, wherein $R^6$ is as defined above;
Y represents an oxygen atom or a sulfur atom; and, where there are two or more groups represented by Y, these are the same or different from each other;
Z represents a group of formula —$COOR^7$, wherein $R^7$ is as defined above, a group of formula —$COR^6$, wherein $R^6$ is as defined above, or a group of formula —$SO_2R^6$, wherein $R^6$ is as defined above;
Q represents a methylene group, an ethylene group or a group of formula —$OCH_2$—;
$R^5$ represents a methyl group, an ethyl group, an isopropyl group or a sec-butyl group; and
X represents: a hydroxy group; an alkanoyloxy group which has from 1 to 5 carbon atoms, and which is unsubstituted or has at least one substituent selected from the group consisting of substituents (d); or a hydroxyimino group;

substituents (a):
halogen atomes, alkoxy groups having from 1 to 4 carbon atoms, alkylthio groups having from 1 to 4 carbon atoms, and alkanoyloxy groups having from 1 to 5 carbon atoms;

substituents (b):
cycloalkyl groups having from 3 to 8 carbon atoms; alkoxy groups having from 1 to 4 carbon atoms; alkylthio groups having from 1 to 4 carbon atoms; cyanoalkylthio groups having from 2 to 5 carbon atoms; alkoxycarbonyl groups having from 2 to 5 carbon atoms; halogen atoms; cyano groups; nitro groups; amino groups; aryl groups which have from 6 to 14 ring carbon atoms and which are unsubstituted or have at least one substitutent selected from the group consisting of substituents (c); aryloxy groups which have from 6 to 14 ring carbon atoms and which are unsubstituted or have at least one substituent selected from the group consisting of substituents (c); and arylthio groups which have from 6 to 14 ring carbon atoms and which are unsubstituted or have at least one substituent selected from the group consisting of substituents (c);

substituents (c):
alkyl groups having from 1 to 4 carbon atoms, alkoxy groups having from 1 to 4 carbon atoms, alkylthio groups having from 1 to 4 carbon atoms, alkanoyloxy groups having from 1 to 5 carbon atoms, alkoxycarbonyl groups having from 2 to 5 carbon atoms, halogen atoms, cyano groups, nitro groups, amino groups, alkylamino groups in which the alkyl parts has from 1 to 4 carbon atoms, dialkylamino groups in which each alkyl part is independently selected from the group consisting of alkyl groups having from 1 to 4 carbon atoms, carbamoyl groups, alkylcarbamoyl groups in which the alkyl part has from 1 to 4 carbon atoms, dialkylcarbamoyl groups in which each alkyl part is independently selected from the group consisting of alkyl groups having from 1 to 4 carbon atoms, and alkanoylamino groups having from 1 to 5 carbon atoms;

substituents (d):
halogen atoms, alkoxy groups having from 1 to 4 carbon atoms, alkoxycarbonyl groups having from 2 to 5 carbon atoms, and carboxy groups.

2. The compound of claim 1, wherein $R^1$ represents a group of formula:

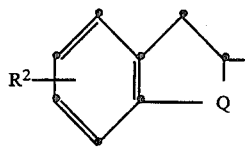

(i)

wherein $R^2$ represents a hydrogen atom or a group of formula —$NR^{9a}COR^{6a}$
wherein:
$R^{9a}$ represents a hydrogen atom or a methyl group;
$R^{6a}$ represents: a hydrogen atom; an alkyl group having from 1 to 4 carbon atoms; a cycloalkyl group having from 3 to 5 carbon atoms; an alkyl group having from 1 to 3 carbon atoms and substituted with a halogen atom, a cyano group, an alkoxy group having from 1 to 3 carbon atoms, an alkylthio group having from 1 to 3 carbon atoms, a cyanomethylthio group or a phenoxy group; an alkenyl group having from 2 to 4 carbon atoms; a phenyl group; a phenyl group substituted with an alkyl grouup having from 1 to 3 carbon atoms, an alkoxy group having from 1 to 3 carbon atoms, a halogen atom or a nitro group; and Q represents a methylene group or an ethylene group.

3. The compound of claim 1, wherein $R^1$ represents a group of formula:

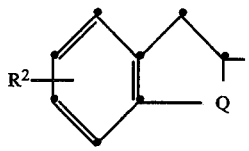

(i)

wherein $R^2$ represents a group of formula:

$R^{6b}$—CO—CO—N($R^{9a}$)— wherein:

$R^{9a}$ represents a hydrogen atom or a methyl group; and $R^{6b}$ represents an alkyl group having from 1 to 4 carbon atoms; a cycloalkyl group having from 3 to 5 carbon atoms; an alkenyl group having from 2 to 4 carbon atoms; a phenyl group; or a phenyl group substituted with an alkyl group having from 1 to 3 carbon atoms, an alkoxy group having from 1 to 3 carbon atoms, a halogen atom or a nitro group.

4. The compound of claim 1, wherein $R^1$ represents a group of formula:

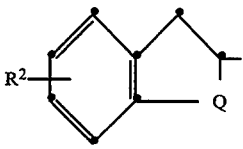

(i)

wherein $R^2$ represents a group of formula:

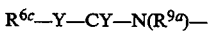

$R^{6c}$—Y—CY—N($R^{9a}$)— wherein:

$R^{9a}$ represents a hydrogen atom or a methyl group;

Y represents an oxygen atom; and $R^{6c}$ represents: an alkyl group having from 1 to 4 carbon atoms; an alkyl group having from 1 to 4 carbon atoms and substituted with a halogen atom or an alkoxy group having from 1 to 3 carbon atoms; a vinyl group; an allyl group; a benzyl group; a methoxybenzyl group; or a nitrobenzyl group.

5. The compound of claim 1, wherein $R^1$ represents a group of formula:

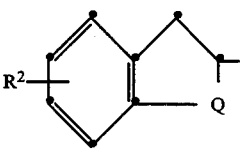

(i)

wherein $R^2$ represents a group of formula:

$R^{6d}$N($R^{6e}$)—CY—N($R^{9a}$)— wherein:

$R^{9a}$ represents a hydrogen atom or a methyl group;

Y represents an oxygen atom or a sulfur atom; and $R^{6d}$ and $R^{6e}$ are the same or different and each represents: a hydrogen atom; an alkyl group having from 1 to 4 carbon atoms; a cycloalkyl group having from 3 to 6 carbon atoms; a phenyl group; or a phenyl group substituted with an alkyl group having from 1 to 3 carbon atoms, an alkoxy group having from 1 to 3 carbon atoms, a halogen atom or a nitro group.

6. The compound of claim 1, wherein $R^1$ represents a group of formula:

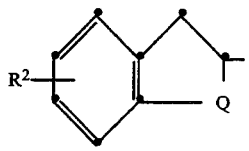

(i)

wherein $R^2$ represents a group of formula:

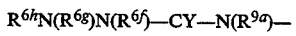

$R^{6h}$N($R^{6g}$)N($R^{6f}$)—CY—N($R^{9a}$)— wherein:

$R^{9a}$ represents a hydrogen atom or a methyl group;

Y represents an oxygen atom; and $R^{6f}$, $R^{6g}$ and $R^{6h}$ are the same or different and each represents: a hydrogen atom; an alkyl group having from 1 to 4 carbon atoms; a cycloalkyl group having from 3 to 6 carbon atoms; a phenyl group; or a phenyl group substituted with an alkyl group having from 1 to 3 carbon atoms, an alkoxy group having from 1 to 3 carbon atoms, a halogen atom or a nitro group.

7. The compound of claim 1, wherein $R^1$ represents a group of formula:

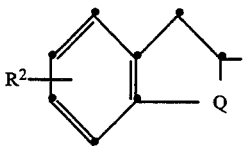

(i)

wherein $R^2$ represents a group of formula:

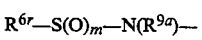

$R^{6r}$—S(O)$_m$—N($R^{9a}$)— wherein:

$R^{9a}$ represents a hydrogen atom or a methyl group;

m is 1 or 2; and $R^{6r}$ represents an alkyl group having from 1 to 4 carbon atoms; an alkyl group having from 1 to 3 carbon atoms group and substituted with a cyano group; a phenyl group; or a phenyl group substituted with an alkyl group having from 1 to 3 carbon atoms, an alkoxy group having from 1 to 3 to carbon atoms, a halogen atom or a nitro group.

8. The compound of claim 1, wherein $R^5$ represents an ethyl group.

9. The compound of claim 1, wherein X represents a hydroxy group.

10. The compound of claim 1, selected from the group consisting of:
13-(5-ethoxycarbonylamino-2-indanyloxy)milbemycin $A_4$ and
13-[5-(3-methylureido)-2-indanyloxy]milbemycin $A_4$ and salts thereof.

11. The compound of claim 1, selected from the group consisting of 13-[5-(3-methylureido)-2-indanyloxy]milbemycin $A_4$.

12. An anthelmintic, acaricidal and insecticidal composition comprising an anthelmintic, acaricidal and insecticidal compound in admixture with a pharmaceutically, argiculturally, veterinarily or horticulturally acceptable carrier or diluent, wherein said compound is selected from the group consisting of the compounds of formula (I) as defined in claim 1.

13. The composition of claim 12, wherein said compound is selected from the group consisting of:
13-(5-ethoxycarbonylamino-2-indanyloxy)milbemycin $A_4$ and
13-[5-(3-methylureido)-2-indanyloxy]milbemycin $A_4$ and salts thereof.

14. A method of treating an animal parasitized by a parasite selected from the group consisting of helminths, acarids and insects by administering thereto at least one compound selected from the group consisting of compounds of the formula (I) as defined in claim 1.

15. The method of claim 14, wherein said compound is selected from the group consisting of:
13-(5-ethoxycarbonylamino-2-indanyloxy)milbemycin $A_4$ and
13-[5-(3-methylureido)-2-indanyloxy]milbemycin $A_4$ and salts thereof.

16. A method of protecting animals or plants from damage by parasites selected from the group consisting of acarids, helminths and insects, which comprises applying an active compound to said animals, to said plants or to seeds of said plants or to a locus including said animals, plants or seeds, wherein the active compound is selected from the group consisting of at least one compound of formula (I) and as defined in claim 1.

17. The method of claim 16, wherein said compound is selected from the group consisting of:
13-(5-ethoxycarbonylamino-2-indanyloxy)milbemycin $A_4$ and
13-[5-(3-methylureido)-2-indanyloxy]milbemycin $A_4$ and salts thereof.

* * * * *

UNITED STATES PATENT AND TRADEMARK OFFICE
CERTIFICATE OF CORRECTION

PATENT NO. : 5,346,918
DATED : September 13, 1994
INVENTOR(S) : MORISAWA et al

It is certified that error appears in the above-identified patent and that said Letters Patent is hereby corrected as shown below:

Title Page: [57] Abstract: Replace the structural formula with the following:

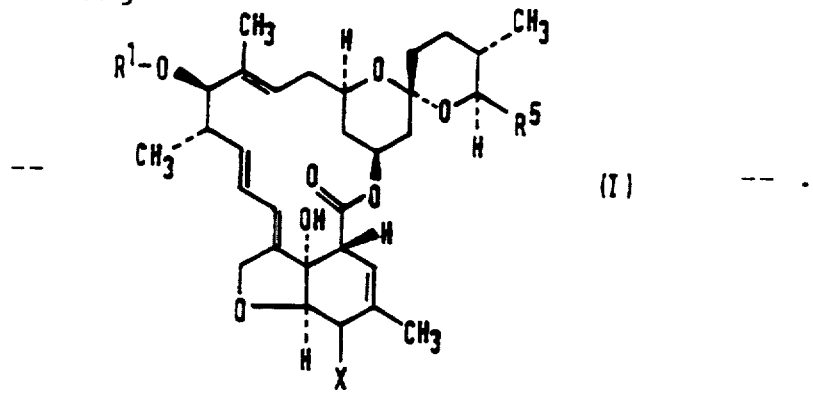

Col. 1, line 13: delete "a".

Col. 1, lines 42-57: replace the structural formula with the following:

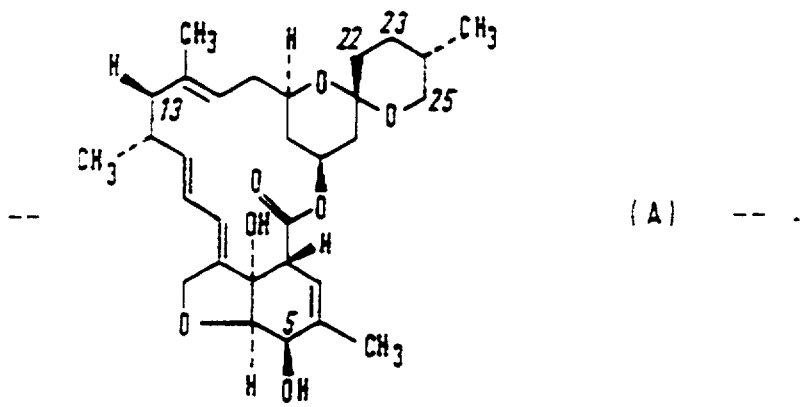

UNITED STATES PATENT AND TRADEMARK OFFICE
CERTIFICATE OF CORRECTION

PATENT NO. : 5,346,918

DATED : September 13, 1994

INVENTOR(S) : MORISAWA et al

It is certified that error appears in the above-identified patent and that said Letters Patent is hereby corrected as shown below:

Col. 3, lines 35-50: replace the structural formula with the following:

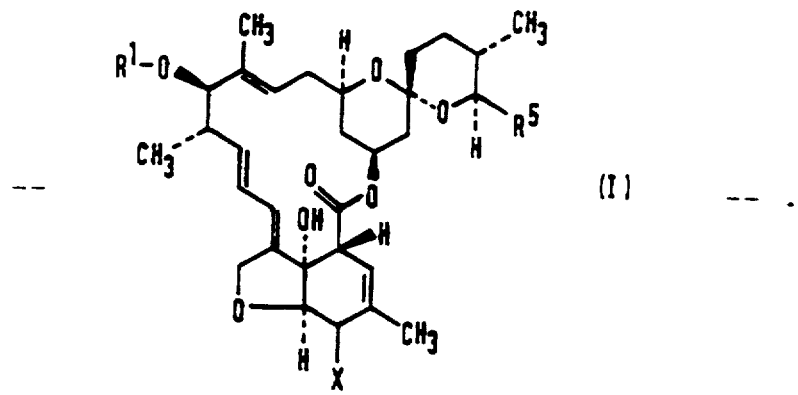

Col. 22, lines 20-33: replace the structural formula with the following:

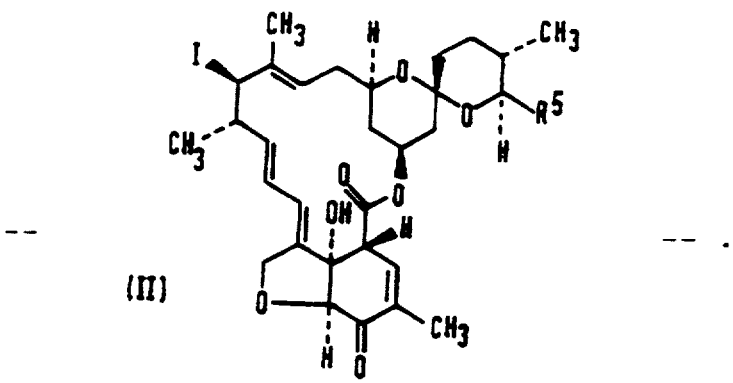

UNITED STATES PATENT AND TRADEMARK OFFICE
CERTIFICATE OF CORRECTION

PATENT NO. : 5,346,918                              Page 3 of 7 pages
DATED      : September 13, 1994
INVENTOR(S): MORISAWA et al It is certified that error appears in the above-identified patent and that said Letters Patent is hereby corrected as shown below:

Columns 23-24, lines 1-33: replace the structural formulas with the following:

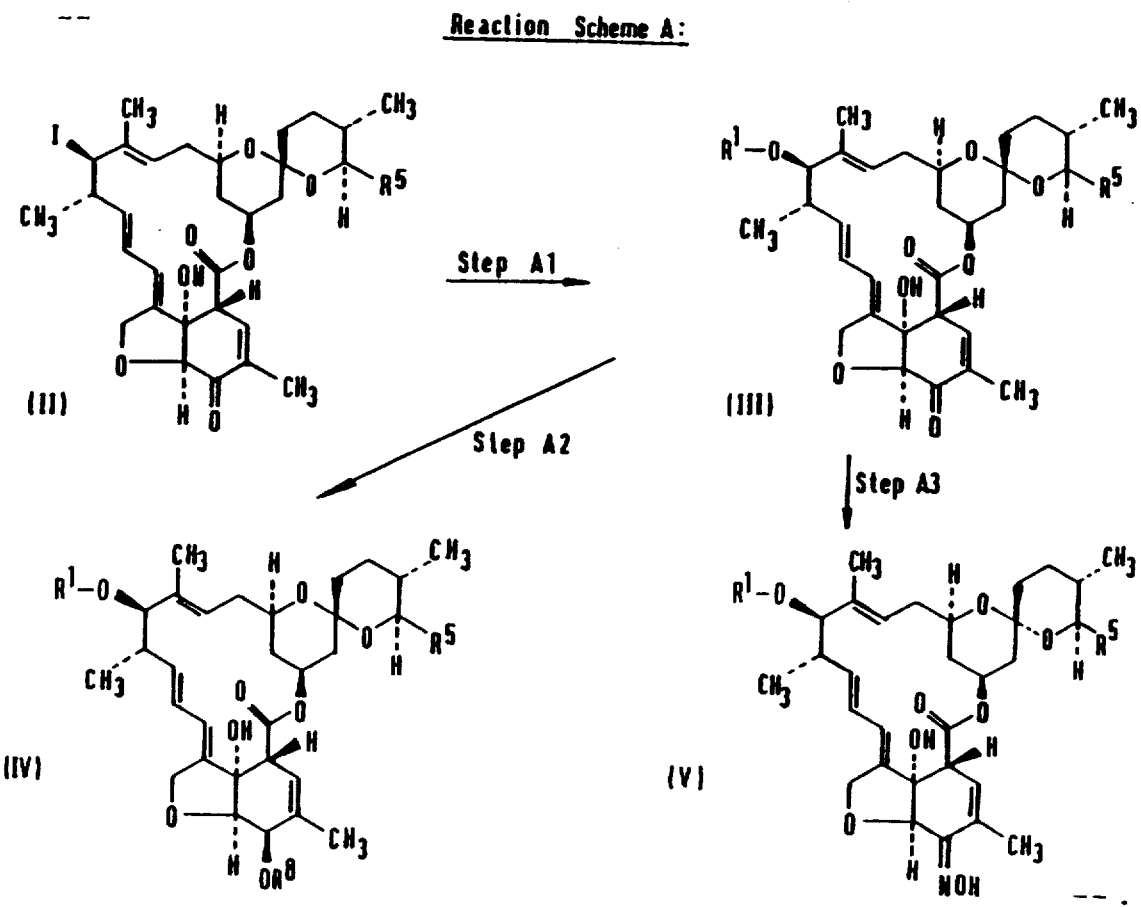

UNITED STATES PATENT AND TRADEMARK OFFICE
CERTIFICATE OF CORRECTION

PATENT NO. : 5,346,918  Page 4 of 7 pages
DATED : September 13, 1994
INVENTOR(S) : MORISAWA et al It is certified that error appears in the above-identified patent and that said Letters Patent is hereby corrected as shown below:

Columns 27-28, lines 1-35: replace the structural formulas with the following:

Reaction Scheme B:

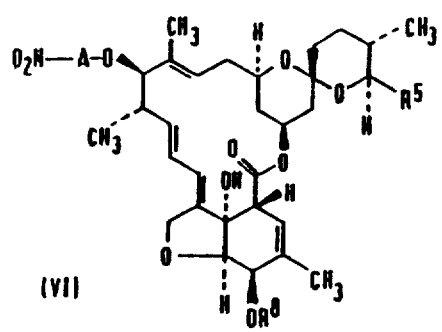
(VII)

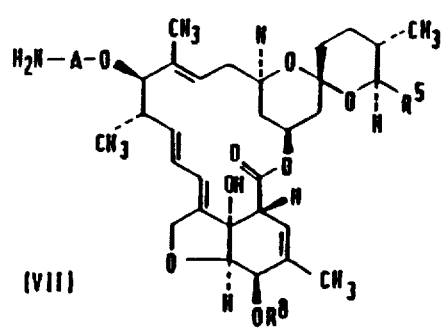
(VIII)

Step B1

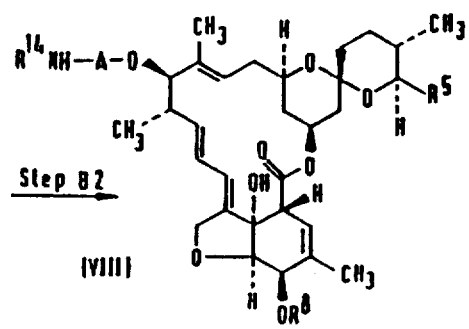
(VIIII)

Step B2

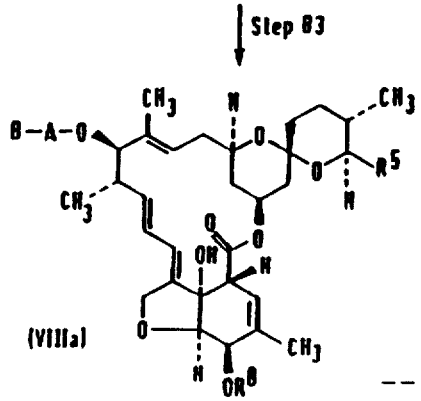
(VIIIa)

Step B3

UNITED STATES PATENT AND TRADEMARK OFFICE
CERTIFICATE OF CORRECTION

PATENT NO. : 5,346,918

DATED : September 13, 1994

INVENTOR(S) : MORISAWA et al

It is certified that error appears in the above-identified patent and that said Letters Patent is hereby corrected as shown below:

Column 31, lines 1-47: replace the structural formulas with the following:

-- Reaction Scheme C:

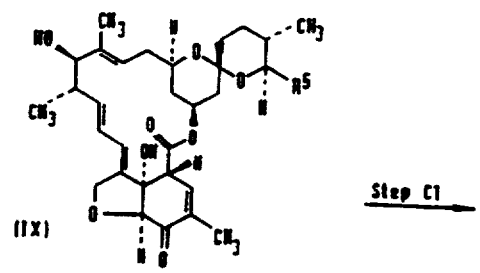

Step C1

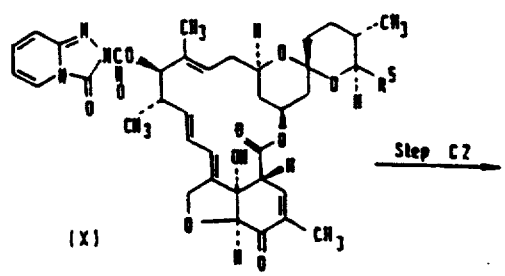

Step C2

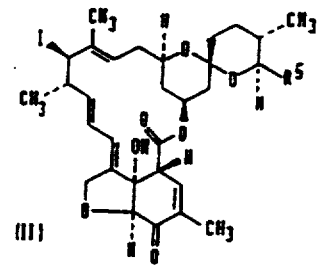

--

UNITED STATES PATENT AND TRADEMARK OFFICE
CERTIFICATE OF CORRECTION

PATENT NO. : 5,346,918

DATED : September 13, 1994

INVENTOR(S) : MORISAWA et al

It is certified that error appears in the above-identified patent and that said Letters Patent is hereby corrected as shown below:

Col. 46, lines 24-38: replace the structural formula with the following:

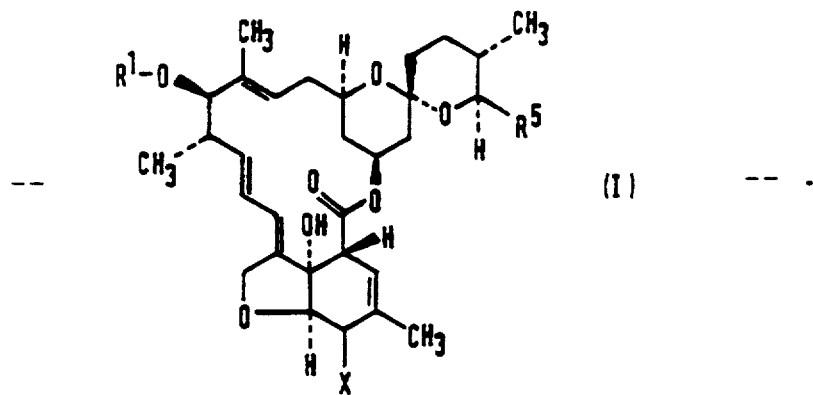

UNITED STATES PATENT AND TRADEMARK OFFICE
CERTIFICATE OF CORRECTION

PATENT NO. : 5,346,918

DATED : September 13, 1994

INVENTOR(S) : MORISAWA et al

It is certified that error appears in the above-identified patent and that said Letters Patent is hereby corrected as shown below:

Col. 51, line 6 (claim 10): delete "and salts thereof".

Col. 51, line 22 (claim 13): delete "and salts thereof".

Col. 52, line 9 (claim 15): delete "and salts thereof".

Col. 52, line 23 (claim 17): delete "and salts thereof".

Signed and Sealed this

Thirteenth Day of February, 1996

BRUCE LEHMAN

*Commissioner of Patents and Trademarks*